US008895759B2

(12) United States Patent
McManus et al.

(10) Patent No.: US 8,895,759 B2
(45) Date of Patent: Nov. 25, 2014

(54) INTERMEDIATES USEFUL IN THE PREPARATION OF MALEIMIDE FUNCTIONALIZED POLYMERS

(71) Applicant: Nektar Therapeutics, San Francisco, CA (US)

(72) Inventors: Samuel P. McManus, Guntersville, AL (US); Antoni Kozlowski, Huntsville, AL (US); Tracy L. Hutchison, New Market, AL (US); Brian Bray, Huntsville, AL (US); Xiaoming Shen, Millbrae, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 14/153,783

(22) Filed: Jan. 13, 2014

(65) Prior Publication Data

US 2014/0128619 A1  May 8, 2014

Related U.S. Application Data

(63) Continuation of application No. 13/568,518, filed on Aug. 7, 2012, now Pat. No. 8,653,286, which is a continuation of application No. 13/233,717, filed on Sep. 15, 2011, now Pat. No. 8,258,324, which is a continuation of application No. 12/822,148, filed on Jun. 23, 2010, now Pat. No. 8,039,579, which is a continuation of application No. 11/004,631, filed on Dec. 3, 2004, now Pat. No. 7,790,835.

(60) Provisional application No. 60/526,752, filed on Dec. 3, 2003.

(51) Int. Cl.
*C07D 207/46* (2006.01)
*C07D 403/12* (2006.01)
*A61K 47/48* (2006.01)
*C08G 65/333* (2006.01)
*C08G 69/08* (2006.01)

(52) U.S. Cl.
CPC ........ *C07D 403/12* (2013.01); *A61K 47/48215* (2013.01); *C08G 65/33337* (2013.01); *C08G 69/08* (2013.01)
USPC .......................................... 548/542; 549/467

(58) Field of Classification Search
CPC ........... C07D 403/12; A61K 47/48215; C08G 65/33337; C08G 69/08
USPC .......................................... 548/542; 549/467
See application file for complete search history.

(56) References Cited

U.S. PATENT DOCUMENTS

| 4,122,076 A | 10/1978 | Jablonski et al. |
| 4,179,337 A | 12/1979 | Davis et al. |
| 4,413,107 A | 11/1983 | Locatelli |
| 4,675,414 A | 6/1987 | DeFusco et al. |
| 4,761,460 A | 8/1988 | Otsuka et al. |
| 4,775,729 A | 10/1988 | DeFusco et al. |
| 5,036,111 A | 7/1991 | Senneron et al. |
| 5,053,423 A | 10/1991 | Liu |
| 5,166,322 A | 11/1992 | Shaw et al. |
| 5,585,484 A | 12/1996 | Acharya et al. |
| 5,629,384 A | 5/1997 | Veronese et al. |
| 5,641,856 A | 6/1997 | Meurs |
| 5,648,506 A | 7/1997 | Desai et al. |
| 5,766,897 A | 6/1998 | Braxton |
| 5,844,020 A | 12/1998 | Paine et al. |
| 5,922,675 A | 7/1999 | Baker et al. |
| 5,932,462 A | 8/1999 | Harris et al. |
| 5,977,163 A | 11/1999 | Li et al. |
| 5,990,237 A | 11/1999 | Bentley et al. |
| 6,180,134 B1 | 1/2001 | Zalipsky et al. |
| 6,180,598 B1 | 1/2001 | Nelson |
| 6,183,738 B1 | 2/2001 | Clark |
| 6,303,119 B1 | 10/2001 | Weisgerber et al. |
| 6,362,254 B2 | 3/2002 | Harris et al. |
| 6,403,753 B1 | 6/2002 | Loy et al. |
| 6,602,498 B2 | 8/2003 | Shen |
| 6,673,905 B2 | 1/2004 | Pozsgay |
| 6,828,401 B2 | 12/2004 | Nho et al. |
| 7,790,835 B2 | 9/2010 | McManus et al. |
| 8,039,579 B2 | 10/2011 | McManus et al. |
| 8,258,324 B2 | 9/2012 | McManus et al. |
| 8,653,286 B2 | 2/2014 | McManus et al. |
| 2001/0044526 A1 | 11/2001 | Shen |
| 2002/0082345 A1 | 6/2002 | Kozlowski et al. |
| 2003/0065134 A1 | 4/2003 | Sakanoue et al. |
| 2003/0162693 A1 | 8/2003 | Winslow et al. |
| 2003/0170474 A1 | 9/2003 | Qiao et al. |
| 2004/0110822 A1 | 6/2004 | McCluskey et al. |
| 2004/0115165 A1 | 6/2004 | Rosen et al. |
| 2004/0167287 A1 | 8/2004 | Kozlowski et al. |

(Continued)

FOREIGN PATENT DOCUMENTS

| DE | 24 33 883 | 2/1976 |
| EP | 0 149 520 | 7/1985 |

(Continued)

OTHER PUBLICATIONS

STIC search.*

(Continued)

*Primary Examiner* — Frances Tischler
(74) *Attorney, Agent, or Firm* — Mark A. Wilson

(57) ABSTRACT

Methods for forming maleimide functionalized polymers are provided. In one such embodiment, a maleimide functionalized polymer is prepared in a method that includes a step of carrying out a reverse Diels-Alder reaction. Intermediates useful in the methods, as well as methods for preparing the intermediates, are also provided. Also provided are polymeric reagents, methods of using polymeric reagents, compounds and conjugates.

4 Claims, No Drawings

(56) References Cited

U.S. PATENT DOCUMENTS

| | | |
|---|---|---|
| 2005/0176922 A1 | 8/2005 | McManus et al. |
| 2010/0261841 A1 | 10/2010 | McManus et al. |
| 2012/0004422 A1 | 1/2012 | McManus et al. |
| 2012/0302761 A1 | 11/2012 | McManus et al. |

FOREIGN PATENT DOCUMENTS

| | | |
|---|---|---|
| EP | 0 251 110 | 1/1988 |
| EP | 0 318 162 | 5/1989 |
| EP | 1 283 233 | 2/2003 |
| FR | 2 031 538 | 11/1970 |
| GB | 1 469 472 | 4/1977 |
| JP | 02 268155 | 11/1990 |
| JP | 03 012414 | 1/1991 |
| JP | 08 041195 | 2/1996 |
| WO | WO 92/16221 | 10/1992 |
| WO | WO 95/11987 | 5/1995 |
| WO | WO 95/34326 | 12/1995 |
| WO | WO 96/32841 | 10/1996 |
| WO | WO 98/27163 | 6/1998 |
| WO | WO 98/30575 | 7/1998 |
| WO | WO 98/31383 | 7/1998 |
| WO | WO 99/03887 | 1/1999 |
| WO | WO 99/64460 | 12/1999 |
| WO | WO 00/05582 | 2/2000 |
| WO | WO 00/21594 | 4/2000 |
| WO | WO 00/62827 | 10/2000 |
| WO | WO 01/62827 | 8/2001 |
| WO | WO 01/68601 | 9/2001 |
| WO | WO 01/84234 | 11/2001 |
| WO | WO 03/047549 | 6/2003 |
| WO | WO 03/059363 | 7/2003 |
| WO | WO 2004/060965 | 7/2004 |
| WO | WO 2004/060966 | 7/2004 |

OTHER PUBLICATIONS

Alam, et al., "The importance of being knotted: effects of the C-terminal knot structure on enzymatic and mechanical properties of bovine carbonic anhydrase II", FEBS Lett., vol. 519, pp. 35-40, (2002).

Bacchi, et al., "Novel Synthetic Polyamines are Effective in the Treatment of Experimental Microsporidiosis, an Opportunistic AIDS-Associated Infection", Antimicrob. Agents and Chemother., vol. 46, No. 1, pp. 55-61, (2002).

Baldwin, et al., "Diastereoselective Diels-Alder Reactions Between Substituted 1,3-Butadienes and N-alpha-Methylbenzylmaleimide", Tetra. Lett., vol. 32, No. 42, pp. 5877-5880, (1991).

Blessing, et al., "Different Strategies for Formation of PEGylated EGF-Conjugated PEI/DNA Complexes for Targeted Gene Delivery", Bioconj. Chem., vol. 12, pp. 529-537, (2001).

Bravo, et al., "Synthesis of Polycyclic Systems Via Diels-Alder Reactions of Sugar Derived Dienes", Heterocycles, vol. 53, No. 1, pp. 81-92, (2000).

Brewer, et al., "Evidence for Possible Nonspecific Reactions between N-Ethylmaleimide and Proteins", Analy. Biochem., vol. 18, pp. 248-255, (1967).

Christakopoulos, et al., "Enhancement of pH-stability of a low molecular mass endoglucanase from *Fusarium oxysporum* by protein pegylation", Carbohy. Res., vol. 314, pp. 95-99, (1998).

Chujo, et al., "Reversible Gelation of Polyoxazoline by Means of Deils-Alder Reaction", Macromolecules, Amer. Chem. Soc., vol. 23, No. 10, pp. 2636-2641, (May 14, 1990).

Dauty, et al., "Intracellular Delivery of Nanometric DNA Particles via the Folate Receptor", Bioconj. Chem., vol. 13, pp. 831-839, (2002).

Frisch, et al., "Synthesis of Short Polyoxyethylene-Based Heterobifunctional Cross-Linking Reagents. Application to the Coupling of Peptides to Liposomes", Bioconj. Chem., vol. 7, No. 2, pp. 180-186, (1996).

Gibson, et al., "The Gabriel Synthesis of Primary Amines", Angew. Chem. internat. Edit., vol. 7, No. 12, pp. 919-930, (1968).

Goodson, et al., "Site-Directed Pegylation of Recombinant Interleukin-2 at its Glycosylation site", Biotech., vol. 8, pp. 343-346, (Apr. 1990).

Gorin, et al., "Kinetics of the Reaction of N-Ethylmaleimide with Cysteine and Some Congeners", Arch. of Biochem. Biophys., vol. 115, pp. 593-597, (1966).

Grigg, et al., "X=Y-ZH Systems as Potential 1,3-Dipoles. Part II. Stereochemistry of 1,3-Dipoles Generated by the Decarboxylative Route to Azomethine Ylides", J. Chem. Soc. Perkin Trans. I., pp. 2693-2701, (1988).

He, et al., "Reducing the Immunogenicity and Improving the In Vivo Activity of Trichosanthin by Site-Directed Pegylation", Life Sci., vol. 65, No. 4, pp. 355-368, (1999).

Hill, et al., "Diels-Alder Bioconjugation of Diene-Modified Oligonucleotides", J. Org. Chem., vol. 66, pp. 5352-5358, (2001).

Juszczak, et al., "UV Resonance Raman Study of β93-Modified Hemoglobin A: Chemical Modifier-Specific Effects and Added Influences of Attached Poly(ethylene glycol) Chains", Biochem., vol. 41, No. 1, pp. 376-385, (2002).

Keller, et al., "Preparation and Some Properties of Maleimido Acids and Maleoyl Derivatives of Peptides", Helvetica Chimica Acta, vol. 58, pp. 531-541, (1975).

Kogan, "The Synthesis of Substituted Methoxy-Poly(Ethylene glycol) Derivatives Suitable for Selective Protein Modification", Synthetic Comm., vol. 22, No. 16, pp. 2417-2424, (1992).

Konopikova, et al., "Synthesis and Fungicidal Activity of Isoxazolines Fused to 3,5- Dichloromaleimide", Collect. Czech. Chem. Commun., vol. 57, pp. 1521-1536, (1992).

Kuehne, et al., "Synthesis and Characterization of Membrane-Active GALA-OKT9 Conjugates", Bioconj. Chem., vol. 12, No. 5, pp. 742-749, (2001).

Lee, et al., "Synthesis and Biological Activities of N-Alaninylmaleimide and its Polymers", J.M.S.-Pure Appl. Chem., A34(1), pp. 1-11, (1997).

Lee, et al., "A new gene delivery formulation of polyethylenimine/DNA complexes coated with PEG conjugated fusogenic peptide", J. of Contr. Rel., vol. 76, pp. 183-192, (2001).

Luo, et al., "Highly Efficient and Thermally Stable Electro-optic Polymer from a Smartly Controlled Crosslinking Process", Adv. Mat., vol. 15, No. 19, pp. 1635-1638, (Oct. 2, 2003).

Makmura, et al., "Development of a Sensitive Assay to Detect Reversibly Oxidized Protein Cysteine Sulfyhdryl Groups", Antioxidants & Redox Signaling, vol. 3, No. 6, pp. 1105-1118, (2001).

Mao, et al., "Chitosan-DNA nanoparticles as gene carriers: synthesis, characterization and transfection efficiency", J. of Contr. Rel., vol. 70, pp. 399-421, (2001).

Metha, et al., "Maleamic and Citraconamic Acids, Methyl Esters, and Imides", J. Org. Chem., vol. 25, pp. 1012-1015, (1960).

Oliver, et al., "Synthesis of Pegylated Immunonanoparticles", Pharm. Res., vol. 19, No. 8, pp. 1137-1143, (Aug. 2002).

Ondrus, et al., "On the use of water as a solvent—simple and short one- step synthesis of maleimides", ARKIVOC, pp. 60-67, (2001).

Ouchi, et al., "Design of Antitumor Agent-Terminated Poly(Ethylene Glycol) Conjugate as Macromolecular Prodrug", Polymer Preprints, vol. 38, No. 1, pp. 582-583, (1997).

Partis, et al., "Cross-Linking of Protein by w-Maleimido Alkanoyl N-Hydroxysuccinimido Esters", J. of Protein Chem., vol. 2, No. 3, pp. 263-277, (1983).

Philp, et al., "Recognition-induced control of a Diels-Alder Reaction", J. Chem. Soc. Chem. Commun., pp. 879-880, (1998).

Renner, et al., "Allynadic-Imides," J. of Polymer Sci., Part A, vol. 27, pp. 1301-1323, (1989).

Roberts, et al., "Chemistry for peptide and protein PEGylation", Adv. Drug Del. Rev., vol. 54, pp. 459-476, (2002).

Romani, et al., "Synthesis of Unsymmetrical Cystine Peptides: Directed Disulfide Pairing with the Sulfenohydrazide Method", Chem. Peptides and Proteins, vol. 2, pp. 29-34, (1984).

Schmidt, et al., "Force Tolerances of Hybrid Nanodevices", Nano Letters, vol. 2, No. 11, pp. 1229-1233, (2002).

(56) References Cited

OTHER PUBLICATIONS

Shaltout, et al, "Maleimide Functionalized Siloxane Resins", Organic/Inorganic Hybrid Materials II. Materials Research Society Symposium, vol. 576, pp. 15-20, (Apr. 5-9, 1999).
Smyth, et al., "Reactions of N-Ethylmaleimide with Peptides and Amino Acids", Biochem. J., vol. 91, pp. 589-595, (1964).
Tang, et al., "Preparation of a New PEGylation Reagent for Sulfhydryl-containing Polypeptide", Tetrahedron Letters, vol. 35, No. 35, pp. 6515-6516, (1994).
Tsutsumi, et al., "Site-specific chemical modification with polyethylene glycol of recombinant immunotoxin anti-Tac(Fv)-PE38 (LMB-2) improves antitumor activity and reduces animal toxicity and immunogenicity", PNAS, vol. 97, No. 15, pp. 8548-8553, (Jul. 18, 2000).
Vargas, et al., "Diels-Alder Modification of Poly(ethylene terephthalate-co-anthracene-2,6-carboxylate) with N-Substituted Maleimides", J. of Polymer Sci: Part A: Polymer Chem., vol. 40, pp. 3256-3263, (2002).
Veronese, "Peptide and protein PEGylation: a review of problem and solutions", Biomaterials, vol. 22, pp. 405-417, (2001).
Walker, "The Mitsunobu Reaction: A Novel Method for the Synthesis of Bifunctional Maleimide Linkers", Tetra. Lett., vol. 35, No. 5, pp. 665-668, (1994).
Wu, et al., "p53 protein oxidation in cultured cells in response to pyrrolidine dithiocarbamate: a novel method for relating the amount of p53 oxidation in vivo to the regulation of p53-responsive genes", Biochem. J., vol. 351, pp. 87-93, (2000).
Zhou, et al., "Synthesis of Glycerophospholipid Conjugates of Cantharidin and its Analogues", Synthetic Commun., vol. 30, No. 19, pp. 3527-3533, (2000).
ACS Registry No. 58914-60-6, (1976).
ACS Registry No. 146226-29-1, (1993).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
NOF Corporation, PEG Derivatives, Phospholipid and Drug Delivery Materials for Pharmaceuticals, 46 pages, Catalogue 2003-1$^{st}$, (Jan. 2003).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
PCT International Search Report corresponding to PCT Application No. PCT/US2004/040712 date of mailing Jul. 4, 2005.
PCT Corrected Version of the Written Opinion of the Searching Authority corresponding to PCT Application No. PCT/US2004/040712 date of mailing Jul. 26, 2005.
International Preliminary Report on Patentability corresponding to PCT Application No. PCT/US2004/040712 date of mailing Jun. 15, 2006.
Enzon Pharmaceuticals, Macromolecular Engineering Technologies, 16 pages, (2004).
NOF Corporation, PEG Derivatives, Phospholipid and Drug Delivery Materials for Pharmaceuticals, 27 pages, Catalogue 2003-2$^{nd}$, (Mar. 2004).
Polypure Products, PEG amines; PEG acids and amino acids; PEG thiols and disulfides; Biotins, 5 pages, (Apr. 2004).

* cited by examiner

INTERMEDIATES USEFUL IN THE PREPARATION OF MALEIMIDE FUNCTIONALIZED POLYMERS

CROSS REFERENCE TO RELATED APPLICATIONS

This application is a continuation of U.S. patent application Ser. No. 13/568,518, filed Aug. 7, 2012, which is a continuation of U.S. patent application Ser. No. 13/233,717, filed Sep. 15, 2011, now U.S. Pat. No. 8,258,324, which is a continuation of U.S. patent application Ser. No. 12/822,148, filed Jun. 23, 2010, now U.S. Pat. No. 8,039,579, which is a continuation of U.S. patent application Ser. No. 11/004,631, filed Dec. 3, 2004, now U.S. Pat. No. 7,790,835, which claims the benefit of priority to U.S. Provisional Patent Application Ser. No. 60/526,752, filed Dec. 3, 2003, the disclosures of which are incorporated herein by reference.

FIELD OF THE INVENTION

This invention relates to methods for preparing water soluble and non-peptidic polymers carrying maleimide functional groups, particularly maleimide-terminated poly(ethylene glycol) polymers.

BACKGROUND OF THE INVENTION

Maleimides are versatile derivatives that find extensive use in chemical synthesis and in biological and pharmacological applications. As Michael acceptors, maleimides react readily with sulfhydryl groups to form stable thioether bonds. This reaction is extensively used with proteins and the like where both sulfhydryl and amine groups are present. At approximately neutral pH, maleimides are highly selective, with sulfhydryl groups being about 1,000 times more reactive than amine groups (Smyth et al., Biochem. J., 91, 589, 1964; Gorin et al. Arch. Biochem. Biophys. 115, 593, 1966; Partis et al., J. Protein Chem, 2, 263-277, 1983). At higher pH values of 8 or above, the reaction of maleimides with amine groups begins to significantly compete (Brewer and Riehm, Anal. Biochem. 18, 248, 1967). While best known as Michael acceptors, maleimides are also useful for their reactivity as dienophiles (Baldwin et al., Tetrahedron Lett., 32, 5877, 1991; Philp and Robertson, J. Chem. Soc., Chem. Commun., 1998, 879; Bravo et al., Heterocycles, 53, 81, 2000) and as dipolarophiles (Grigg et al., J. Chem. Soc., Perkin Trans. 1, 1988, 2693; Konopikova et al., Collect. Czech. Chem. Commun., 57, 1521, 1991; Philp and Booth, Tetrahedron Lett., 39, 6987, 1998).

Maleimide groups can be used to facilitate covalent attachment of proteins and other molecules to polymers. For example, the hydrophilic polymer poly(ethylene glycol), abbreviated PEG, is often used to conjugate bioactive molecules and render them soluble in aqueous media (Harris and Zalipsky, "Poly(Ethylene Glycol) Chemistry and Biological Applications", ACS Symposium Series, ACS, Washington, D.C., 1997). PEG-maleimide is an example of a reactive polymer suitable for reaction with thiol or amino groups on a biologically active molecule.

Many of the methods for preparing PEG maleimides involve connecting an activated PEG to a small linker molecule comprising a maleimide group, many of which are available commercially. There are a variety of shortcomings associated with several known PEG maleimides and methods for their production. For example, the so-called "linkerless" PEG maleimides, which have no linker group between the PEG and the maleimide group, are often prepared directly from a PEG amine using one of two methods. See U.S. Pat. No. 6,602,498. These methods, however, generally result in a relatively impure product inasmuch as a fairly significant amount of an open ring maleamic acid-containing derivative is present in the final product as will be discussed below.

In the first method disclosed in U.S. Pat. No. 6,602,498, a water soluble and non-peptidic polymer backbone is reacted with maleic anhydride to form an open ring amide carboxylic acid intermediate (a maleamic acid intermediate). The ring of the intermediate is then closed in a second step by heating the intermediate in the presence of acetic anhydride and a salt of acetic acid, such as sodium or potassium acetate, to a temperature of about 50° C. to about 140° C. for about 0.2 to about 5 hours. This two-step process is summarized in the reaction scheme below:

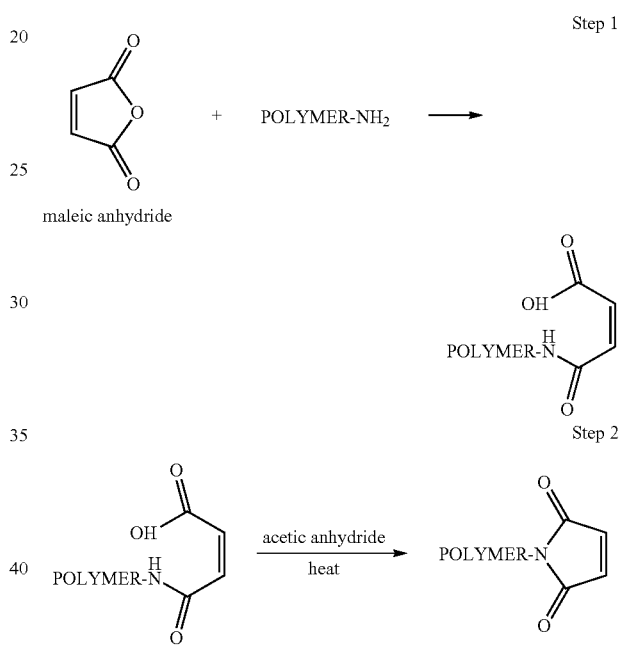

The crude N-maleimidyl polymer product made by this method may contain a substantial amount of the open ring maleamic acid intermediate. A major cause for the appearance of the open ring maleamic acid intermediate may lie with the heating step, especially if any acidic species is generated or is a contaminant in the acetic anhydride. Under these conditions, it is possible to isomerize the C=C bond and thus make ring closure difficult, if not impossible. As a result, it is desirable to purify the polymer product by some method, such as ion exchange chromatography, capable of removing the impurity. However, the maleimide ring system does not tolerate a chromatographic column bearing basic or nucleophilic sites, thus making purification more difficult. A second problem with this synthetic route stems from the use of PEG amine. PEG amines are routinely contaminated with a small amount of secondary amine, which results in a product impurity that is difficult to remove.

Similarly, Sakanoue et al., US 2003/0065134 A1, describe a related method except the PEG-maleimides produced therein comprise a propylene group rather than an ethylene group between the ultimate PEG oxygen and the maleimide nitrogen. The Sakanoue method suffers from the same problems as mentioned above. Further, the reference teaches that the PEG amines are generally manufactured by reduction of a nitrile group using hydrogen and a nickel catalyst, which can lead to the introduction of additional impurities due to reaction between the amine product and an imine intermediate.

In a second synthetic route described in U.S. Pat. No. 6,602,498, an N-alkoxycarbonylmaleimide is reacted with a polymeric amine to form an N-maleimidyl polymer product. A ring-opening and ring-closing reaction occurs similar to the one described above. Again, during the course of the reaction, especially with heating, it is possible to isomerize the C=C bond of the maleamic acid and thus make ring closure difficult, if not impossible. Therefore, again, the reaction may not proceed to completion and purification of the crude product would be required in order to obtain a highly pure maleimide. Again, chromatography is not a viable option because of the sensitivity of the maleimide group to the functional groups of the ion exchange column. As with the previously described synthetic routes, this method suffers from the use of PEG amines, which contain secondary amines that cannot readily be removed.

There is a need in the art for alternative methods for preparing maleimide terminated polymers in high yield and free from significant amounts of polymer impurities, particularly significant amounts of polymer impurities that cannot be readily removed using conventional purification techniques, such as ion exchange chromatography.

SUMMARY OF THE INVENTION

The present invention provides a polymer comprised of a water soluble and non-peptidic polymer covalently attached (either directly or through one or more atoms) to at least one Diels-Alder adduct. The Diels-Alder adduct is capable of readily undergoing a retro or reverse Diels-Alder reaction, which is a reverse [4+2] cycloaddition process, that results in release of an acyclic or alicyclic diene and formation of a maleimide group attached to the polymer. As used herein, a Diels-Alder adduct that is capable of "readily" undergoing a retro or reverse Diels-Alder reaction means a Diels-Alder adduct that can undergo such a reaction in conditions of temperature, pH, concentration, and the like, without substantially disrupting the covalent bond though which the water soluble and non-peptidic polymer is attached. Such conditions can be determined experimentally.

The Diels-Alder adduct typically comprises an imide ring (i.e., a ring of atoms comprising an imide functionality), such as a bicyclic or polycyclic imide ring. It is preferred, however, that the imide ring is a tricyclic imide ring. With respect to the size of the imide ring, the Diels-Alder adduct will typically comprise about 10 to about 20 total ring atoms and one or two heteroatoms in one or more of the rings.

Among other things, the water soluble and non-peptidic polymer covalently attached to at least one Diels-Alder adduct represents a useful polymer intermediate that—when used in a synthetic procedure to prepare maleimide functionalized polymers in the method described herein—obviates the problems associated with other synthetic methods that involve ring-opening/ring-closing steps that lead to yield-reducing isomerization. As a result, maleimide functionalized polymers can now be prepared without requiring elaborate and costly purification steps.

The polymer intermediate (comprising a water soluble and non-peptidic polymer covalently attached to at least one Diels-Alder adduct) can undergo a retro Diels-Alder reaction. The retro Diels-Alder reaction will result in both a maleimide functionalized polymer and a diene. The diene released during the retro Diels-Alder reaction will vary depending on the structure of the Diels-Alder adduct. Examples of such dienes include 1,3-butadiene, 1,3-cyclohexadiene, 1,3-cycloheptadiene, benzene, anthracene, isobenzofuran, isoindole, isophosphindole, thiophene, and selenophene, wherein the diene may be substituted or unsubstituted at each atom position. Dienes that are cyclic in nature are particularly preferred, wherein the diene may be substituted or unsubstituted at each ring atom position. In this regard, preferred cyclic dienes that may be released as a result of the reaction include cyclopentadiene, pyrrole and furan.

In one aspect, the invention provides a polymer intermediate having the structure:

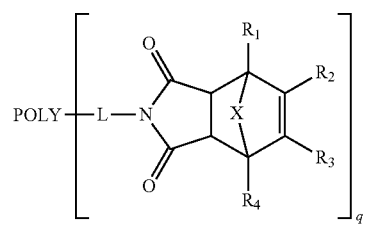

wherein:
X is an optional alkylene, substituted alkylene, alkenylene, substituted alkenylene, arylene, substituted arylene, —C(O)—, heteroatom (such as —NH—) or substituted heteroatom (such as an N-alkyl and N-aryl);

each of $R_1$, $R_2$, $R_3$ and $R_4$ is independently selected from the group consisting of H, halo, hydroxyl, carboxyl, carboxylalkyl, thiol, alkylthio, acyl, acyloxy, nitro, cyano, azido, trihalomethyl, alkyl, substituted alkyl, cycloalkyl, substituted cycloalkyl, alkoxy, aryl, substituted aryl, heterocycle, substituted heterocycle, heteroaryl, and substituted heteroaryl, or $R_2$ and $R_3$, together with the carbon atoms attached thereto, form a 6-membered aryl ring (i.e., a benzene ring);

POLY is a water soluble and non-peptidic polymer;
L is an optional linkage; and
q is an integer of 1 to about 100.

The linkage between the polymer and the Diels-Alder adduct is preferably hydrolytically stable. One exemplary linkage, L, comprises a saturated acyclic, alicyclic or mixed acyclic/alicyclic hydrocarbon chain adjacent to the nitrogen atom of the Diels-Alder adduct, the hydrocarbon chain comprising a bivalent saturated cycloalkyl group, an alkylene group, or a combination thereof, and having a total number of carbons ranging from 1 to about 30. Preferably, the linkage, L, has the structure -$L_1$-$L_2$-, wherein $L_1$ is a hydrolytically stable linkage adjacent to the polymer (e.g., a heteroatom linkage, an amide linkage, an amine linkage, a urethane linkage, or a urea linkage, optionally including an alkylene chain or an ethylene oxide oligomer) and $L_2$ is the hydrocarbon chain portion of the linkage adjacent to the Diels-Alder adduct. Exemplary $L_2$ structures include —$(CR_5R_6)_m$— or —$(CR_5R_6)_p$—C3-C12cycloalkyl-$(CR_5R_6)_q$—, wherein each of $R_5$ and $R_6$ is independently H, alkyl, or cycloalkyl, m is 1 to about 20, and each of p and q is independently 0 to about 10.

The water soluble and non-peptidic polymer, POLY, is preferably poly(ethylene glycol), although other polymers could also be used, such as other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxyacetic acid), poly(acrylic acid), poly(vinyl alcohol), polyphosphazene, polyoxazolines, and poly(N-acryloylmorpholine). The polymer can have any of a variety of geometric configurations, such as a linear configuration (e.g., mPEG or difunctional PEG) or a multi-arm or branched configuration (e.g., a polyol core attached to a plurality of polymer arms radiating out from the core).

In another aspect, the invention provides a composition comprising at least about 80%, more preferably at least about 85%, still more preferably at least about 90%, yet still more preferably at least about 95%, still more preferably at least about 96%, still more preferably at least about 97%, yet still more preferably at least about 98%, and most preferably at least about 99% by weight of a plurality of polymers, each polymer in the plurality comprised of a maleimide functionalized polymer (i.e., a polymer covalently attached to at least one maleimide group).

In a further aspect, the invention provides a method of forming a polymer intermediate useful in the synthesis of a maleimide functionalized polymer, the method comprising:

i) providing a water soluble and non-peptidic polymer comprising at least one functional group; and ii) reacting the functional group of the polymer with a Diels-Alder adduct reagent comprising a polycyclic imide ring or a polycyclic anhydride ring to form a polymer intermediate comprising a Diels-Alder adduct.

In one embodiment of the method of the invention, the Diels-Alder adduct reagent comprises a polycyclic anhydride ring and the functional group of the polymer is an amine group. An exemplary polycyclic anhydride ring has the structure:

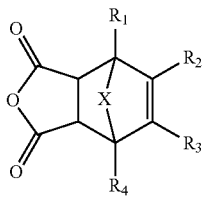

wherein each of X, $R_1$, $R_2$, $R_3$ and $R_4$ is as previously defined.

In another embodiment of the method of the invention, the Diels-Alder adduct reagent comprises a polycyclic imide ring and the functional group of the polymer is reactive with a nucleophilic salt of an imide in a nucleophilic substitution reaction. An exemplary salt of a polycyclic imide ring has the structure:

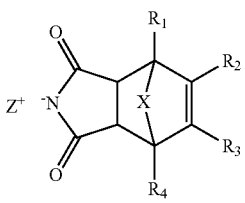

wherein $Z^+$ is a counter ion, and each of X, $R_1$, $R_2$, $R_3$ and $R_4$ is as previously defined.

In yet another embodiment of the method of the invention, where a more complex linkage between the polymer and the Diels-Alder adduct is desired, the Diels-Alder adduct reagent has the structure:

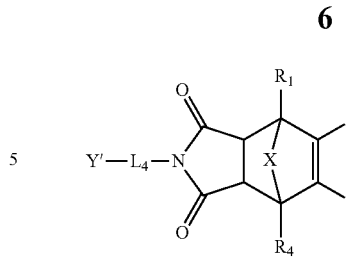

wherein:

Y' is a functional group reactive with a functional group of the polymer;

$L_4$ is a hydrolytically stable linkage; and each of X, $R_1$, $R_2$, $R_3$ and $R_4$ is as previously defined.

In a further embodiment providing a more complex linkage between the polymer and the Diels-Alder adduct, the polymer has the formula POLY-$L_3$-Y, wherein POLY is a water soluble and non-peptidic polymer, $L_3$ is a hydrolytically stable linkage, and Y is a functional group reactive with the Diels-Alder adduct reagent, such as an amino group.

Note that the linkage, L, between the polymer and the Diels-Alder adduct (and ultimately between the polymer and the maleimide group) is defined by the structure of the Diels-Alder adduct reagent and the polymer reagent. For example, the linkage can be defined by the -$L_3$-Y structure of the polymer described above, by the -$L_4$-Y' structure of the Diels-Alder adduct reagent described above, or by a combination thereof. Linkages formed from a combination of $L_3$ and $L_4$ (each of $L_3$ and $L_4$ associated with a different molecule), however, do not typically include all the atoms of $L_3$ and $L_4$ due to the chemistry involved. For example, one of $L_3$ or $L_4$ may include a leaving group that cleaves as $L_3$ and $L_4$ become coupled.

In another aspect, the invention provides a method of forming a maleimide functionalized polymer by treating the polymer intermediate described herein under conditions sufficient to initiate a retro Diels-Alder reaction, wherein a diene is released, thereby resulting in maleimide functionalized polymer.

In one embodiment involving formation of a maleimide group from a Diels-Alder adduct prior to reaction with a polymer, the method comprises:

i) providing a linker molecule comprising a hydrocarbon chain, the hydrocarbon chain comprising a bivalent saturated cycloalkyl group, an alkylene group, or a combination thereof, and having a total number of carbons ranging from 1 to about 30;

ii) reacting the linker molecule with a Diels-Alder adduct comprising a polycyclic imide ring or a polycyclic anhydride ring to form a Diels-Alder adduct linker;

iii) treating the Diels-Alder linker under conditions sufficient to initiate a retro Diels-Alder reaction, optionally in the presence of a reactive dienophile, wherein a diene is released from the Diels-Alder adduct to form a maleimide functionalized linker; and iv) reacting a water soluble and non-peptidic polymer with the maleimide functionalized linker to form a maleimide functionalized polymer.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. DEFINITIONS

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG" or "polyethylene glycol," as used herein, is meant to encompass any water soluble poly(ethylene oxide). Typically, PEGs for use in the present invention will comprise one of the two following structures: "—O(CH$_2$CH$_2$O)$_m$—" or "—CH$_2$CH$_2$O(CH$_2$CH$_2$O)$_m$—CH$_2$CH$_2$—," where (m) is 3 to 3000, and the terminal groups and architecture of the overall PEG may vary. "PEG" means a polymer that contains a majority, that is to say, greater than 50%, of subunits that are —CH$_2$CH$_2$O—. One commonly employed PEG is end-capped PEG. When PEG is defined as "—O(CH$_2$CH$_2$O)$_m$—" the end capping group is generally a carbon-containing group typically comprised of 1-20 carbons and is preferably alkyl (e.g., methyl, ethyl, butyl or benzyl) although saturated and unsaturated forms thereof, as well as aryl, heteroaryl, cyclo, heterocyclo, and substituted forms of any of the foregoing are also envisioned. When PEG is defined as "—CH$_2$CH$_2$O (CH$_2$CH$_2$O)$_m$—CH$_2$CH$_2$—," the end capping group is generally a carbon-containing group typically comprised of 1-20 carbon atoms and an oxygen atom that is covalently bonded to the group and is available for covalently bonding to one terminus of the PEG. In this case, the group is typically alkoxy (e.g., methoxy, ethoxy, butyloxy or benzyloxy) and with respect to the carbon-containing group can optionally be saturated and unsaturated, as well as aryl, heteroaryl, cyclo, heterocyclo, and substituted forms of any of the foregoing. The other ("non-end-capped") terminus is a typically hydroxyl, amine or an activated group that can be subjected to further chemical modification when PEG is defined as "—CH$_2$CH$_2$O(CH$_2$CH$_2$O)$_m$—CH$_2$CH$_2$—." In addition, the end-capping group can also be a silane. Specific PEG forms for use in the invention include PEGs having a variety of molecular weights, structures or geometries (e.g., branched, linear, forked PEGs, multifunctional, and the like), to be described in greater detail below.

The end-capping group can also advantageously comprise a detectable label. When the polymer has an end-capping group comprising a detectable label, the amount or location of the polymer and/or the moiety (e.g., active agent) to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like.

Molecular weight in the context of a water soluble polymer of the invention, such as PEG, can be expressed as either a number average molecular weight or a weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-pint depression, boiling-point elevation, or osmotic pressure) to determine number average molecular weight or the use of light scattering techniques, ultracentrifugation or viscometry to determine weight average molecular weight. The polymeric reagents of the invention are typically polydisperse (i.e., number average molecular weight and weight average molecular weight of the polymers are not equal), possessing low polydispersity values of preferably less than about 1.05.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., *Protective Groups in Organic Synthesis*, 3rd ed., John Wiley & Sons, New York, N.Y. (1999).

As used herein, the term "functional group" or any synonym thereof is meant to encompass protected forms thereof.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 2-methylbutyl, 2-methylpropyl (isobutyl), 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, such as ethynyl, n-propynyl, isopentynyl, n-butynyl, octynyl, decynyl, and so forth.

"Alkoxy" refers to an —O—R group, wherein R is alkyl or substituted alkyl, preferably C1-C20 alkyl (e.g., methoxy, ethoxy, propyloxy, benzyloxy, etc.), preferably C1-C7.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: C3-C8 cycloalkyl, e.g., cyclopropyl, cyclobutyl, and the like; halo, e.g., fluoro, chloro, bromo, and iodo; cyano; alkoxy; phenyl; substituted phenyl; and the like.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Substituted aryl" is aryl having one or more non-interfering groups as a substituent. For substitutions on a phenyl ring, the substituents may be in any orientation (i.e., ortho, meta, or para).

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heterocycle" is a heterocycle having one or more side chains formed from non-interfering substituents.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Substituted heteroaryl" is heteroaryl having one or more non-interfering groups as substituents.

"Heteroatom" refers to any atom other than hydrogen or carbon in a hydrocarbon analog compound. Examples include oxygen, sulfur, nitrogen, phosphorus, arsenic, silicon, selenium, tellurium, tin, and boron.

"Electrophile" refers to an ion or atom or a neutral or ionic collection of atoms, having an electrophilic center, i.e., a center that is electron seeking, capable of reacting with a nucleophile.

"Nucleophile" refers to an ion or atom or a neutral or ionic collection of atoms, having a nucleophilic center, i.e., a center that is seeking an electrophilic center or capable of reacting with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, orthoesters, and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a PEG-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

A "difunctional" polymer means a polymer having two functional groups contained therein, either the same (i.e., homodifunctional) or different (i.e., heterodifunctional).

A basic or acidic reactant described herein includes neutral, charged, and any corresponding salt forms thereof.

The term "patient," refers to a living organism suffering from or prone to a condition that can be prevented or treated by administration of a conjugate, and includes both humans and animals.

"Optional" or "optionally" means that the subsequently described circumstance may or may not occur, so that the description includes instances where the circumstance occurs and instances where it does not.\

Unless otherwise noted, molecular weight is expressed herein as number average molecular weight ($M_n$), which is defined as $$\frac{\sum N_i M_i}{\sum N_i},$$

wherein Ni is the number of polymer molecules (or the number of moles of those molecules) having molecular weight Mi.

The term, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

As used herein, "composition substantially lacks water soluble and non-peptidic polymers covalently attached to a maleamic acid group" means a composition that lacks less than 3%, more preferably less than 2%, still more preferably less than 1%, and most preferably less than 0.5%, by weight, of water soluble and non-peptidic polymers covalently attached to a maleamic acid group.

The phrase "covalently attached" encompasses both direct covalent attachment, as well as covalent attachment through one or more atoms.

II. METHOD OF PREPARING MALEIMIDE FUNCTIONALIZED POLYMERS

In one aspect, the present invention provides a method for forming a maleimide functionalized polymer that involves use of a Diels-Alder adduct as a maleimide precursor, the Diels-Alder adduct being covalently attached (either directly or through one or more atoms) to either (i) a water soluble and non-peptidic polymer, or (ii) a linker molecule suitable for attachment to a water soluble and non-peptidic polymer. As used herein, a Diels-Alder adduct refers to a cyclic structure capable of undergoing a reverse or retro Diels-Alder reaction that fractures the adduct into a maleimide group that remains attached to the polymer or linker molecule and a diene, which is released from the adduct. The Diels-Alder adduct is typically a structure formed by a cycloaddition reaction between a conjugated diene and a dienophile (i.e., a Diels-Alder reaction).

Because the method of the invention utilizes a maleimide precursor that comprises a rigid ring system and the reverse Diels-Alder reaction does not involve ring opening/ring closing steps of the ultimate maleimide ring, isomerization of the type that leads to a maleamic acid impurity does not occur and the final product is not contaminated with an open ring compound (i.e., a maleamic acid intermediate). As a result, a highly pure product can be provided without the need for expensive purification steps, such as ion exchange chromatography.

In one embodiment, the method of the invention comprises reaction of a water soluble and non-peptidic polymer having one or more functional groups (the "polymer starting material") with a Diels-Alder adduct reagent having a complementary functional group to form a polymer intermediate comprising a Diels-Alder adduct.

The Diels-Alder adduct reagent typically comprises a bicyclic or polycyclic imide (with tricyclic imides being most preferred) or a bicyclic or polycyclic anhydride (with tricyclic anhydrides being most preferred).

The polymer starting material has one or more available functional groups suitable for reaction with the Diels-Alder adduct reagent to form the polymer intermediate. The type of functional group present on the polymer starting material can vary and will depend, in part, on the structure of the Diels-Alder adduct reagent. The functional groups on each component must be complementary.

For example, if the Diels-Alder adduct reagent comprises a salt of an imide then it will act as a nucleophile in a reaction with a polymer bearing an electrophilic functional group. The electrophilic functional group may react with a loss of a leaving group so as to allow for nucleophilic substitution. Exemplary functional groups for this reaction include halogens (e.g., bromo, chloro, and iodo), sulfonate ester (e.g., methanesulfonate ester, trifluoromethanesulfonate ester, trichloromethanesulfonate ester, 2,2,2-trifluoroethanesulfonate ester, 2,2,2-trichloroethanesulfonate ester, nonafluorobutanesulfonate ester, p-bromobenzenesulfonate ester, p-nitrobenzenesulfonate ester, and p-toluenesulfonate ester), active esters (e.g., N-hydroxysuccinimidyl ester and 1-benzotriazolyl ester), and active carbonate (e.g., N-hydroxysuccinimidyl carbonate, 1-benzotriazolyl carbonate, p-nitrophenyl carbonate).

In addition, the polymer can include an active ester and thus undergo a nucleophilic substitution at a carbonyl group, although this mode of reaction is not generally preferred when a nucleophilic nitrogen is a part of the Diels-Alder adduct reagent. Also, the nucleophilic nitrogen of the Diels-Alder adduct reagent in this embodiment could add to the beta carbon of an electrophilic alpha, beta-unsaturated system, such as a polymer containing a terminal acrylamide, maleimide, vinyl sulfone or vinyl ketone group, thereby further limiting the usefulness of this approach when a polymer containing such a group is used.

Furthermore, the amino group of an amine-bearing polymer can act as a nucleophilic component and an anhydride of an anhydride-bearing Diels-Alder adduct reagent can serve as an electrophilic component.

In still yet another scenario, a linker can initially be attached to the nucleophilic nitrogen of the Diels-Alder adduct reagent. In this case, the linker includes a functional group that can ultimately react with a complementary functional group present on a polymer. Advantageously, the functional group now attached to the Diels-Alder adduct reagent can be electrophilic or nucleophilic, depending on the functional group associated with the polymer, as previously discussed.

Thus, suitable functional groups for reacting linkers, reagents (e.g., polymers, Diels-Alder adduct reagents), and so forth are known or can be determined experimentally by one of ordinary skill in the art.

The initial coupling step that results in covalent linking of the polymer to the Diels-Alder adduct preferably occurs at a temperature of about 20 to about 80° C. The exact process conditions to be utilized will depend, in part, on the functional groups on the polymer and Diels-Alder adduct involved in the reaction. For any given functional group and Diels-Alder adduct, one or ordinary skill in the art can determine experimentally whether any given set of conditions is sufficient for the coupling step.

Having formed the polymer intermediate comprised of a water soluble and non-peptidic polymer covalently attached to at least one Diels-Alder adduct, the polymer intermediate can be subjected to conditions sufficient to initiate a retro Diels-Alder reaction. The retro Diels-Alder reaction results in release of a diene from the Diels-Alder adduct, thereby providing a maleimide functionalized polymer.

Typically, the retro Diels-Alder reaction conditions require heat. Thus, the polymer intermediate is heated to a temperature of about 60 to about 160° C. The exact temperature needed will depend on the structure of the Diels-Alder adduct and can be determined experimentally.

Diels-Alder adducts that require relatively low temperatures (e.g., about 60 to about 130° C.) to liberate the diene component of the adduct are preferred. For example, where the liberated diene is furan, the retro Diels-Alder reaction occurs readily at around 110° C. While the most preferred diene components, such as furan and 1,3-cyclopentadiene, have relatively low boiling points and can be distilled free of the reaction components once liberated, some dienes are not readily distilled away. In the latter case, one may optionally add a reactive dienophile, such as maleic anhydride, to the reaction mixture. The dienophile will undergo an exchange reaction with the polymeric adduct. Generally, for this to work effectively, the new Diels-Alder adduct formed in the trapping reaction with the added dienophile must be more stable than the Diels-Alder adduct undergoing the retro Diels-Alder reaction, or a substantial excess of the reactive dienophile should be added.

The schematic labeled as "Reaction Scheme I" shows an exemplary approach in accordance with the above discussion. In this scheme, a polymer comprising a leaving group ("LG") and a salt of an imide (shown as the potassium salt of a tricyclic amide) are reacted via nucleophilic substitution to form a polymer intermediate, which is then followed by a reverse Diels-Alder reaction to provide a maleimide functionalized polymer and furan.

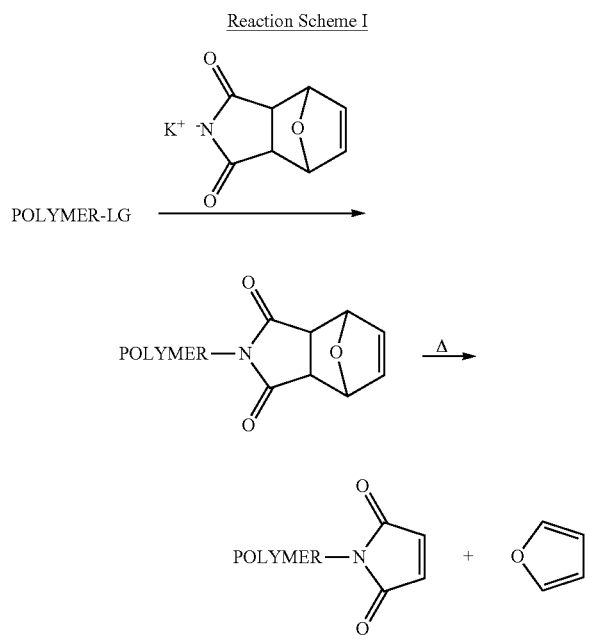

Another exemplary approach is depicted schematically in "Reaction Scheme II." In this scheme, the terminated nitrogen atoms of two amine groups attached to a polymer are effectively "doubly acylated" by an anhydride-containing Diels-Alder adduct reagent (shown as the tricyclo anhydride "7-oxabicyclo[2.2.1]hept-5-ene-2,3-dicarboxylic anhydride"), thereby forming a polymer intermediate. Thereafter, a retro Diels-Alder reaction is carried out to provide a maleimide functionalized polymer and furan. Although shown with a diamino polymer, the approach can be carried out with polymers bearing 1, 3, 4, 5, 6 or more amino groups.

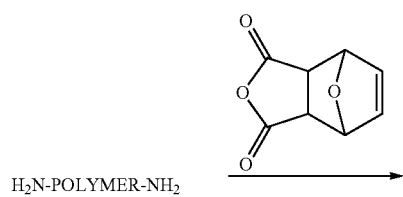

The reactions shown above in Reaction Schemes I and II utilize relatively simple functionalized polymers and Diels-Alder adduct reagents that react to form so-called "linkerless" maleimides, meaning the maleimide group is directly attached to the polymer. Thus, for example, when the polymer is PEG, the maleimide group is directly attached to the terminal ethylene group of the PEG polymer without any other intervening linkage. If desired, however, more complex linkages can be formed using the method of the invention by utilizing either a functionalized polymer or a Diels-Alder adduct reagent that further comprises a more complex linkage structure. In certain applications, it is desirable to form maleimide functionalized polymers having a linkage between the maleimide and the polymer that imparts a greater degree of hydrolytic stability to inhibit ring opening of the maleimide ring in aqueous solution.

Reaction Scheme III below illustrates an exemplary embodiment of the method of the invention that involves modification of the polymer starting material to incorporate a linkage comprising a cycloalkyl group (although other alkyl groups can also be used). As shown, a readily available activated PEG ester is reacted with a monoprotected diamine to yield a protected PEG amine. Deprotection (using art-known methods) gives a PEG amine that includes a terminal cycloalkyl structure. Thereafter, the PEG amine can be reacted with a commercially available tricyclic anhydride to form a polymer intermediate. The polymer intermediate, in turn, is heated to effect the retro Diels-Alder reaction to thereby produce the maleimide functionalized polymer and furan. Because furan has a relatively low boiling point, it vaporizes out of the reaction medium at the temperatures used effect the retro Diels-Alder reaction. The result is formation of a PEG maleimide comprising a cycloalkyl-containing linker that imparts hydrolytic stability to the maleimide and to conjugates of the maleimide. As this maleimide is more stable to hydrolysis than linkerless forms, this reaction sequence can be carried out in either aqueous or non-aqueous solvents. However, non-aqueous solvents are preferred to minimize the possibility of ring-opening. Note that although Reaction Scheme III involves modification of the polymer to incorporate the desired linkage structure prior to reaction with the Diels-Alder adduct reagent, the invention also encompasses modification of the Diels-Alder adduct reagent to include a linkage structure prior to reaction of the adduct with the polymer.

Reaction Scheme III

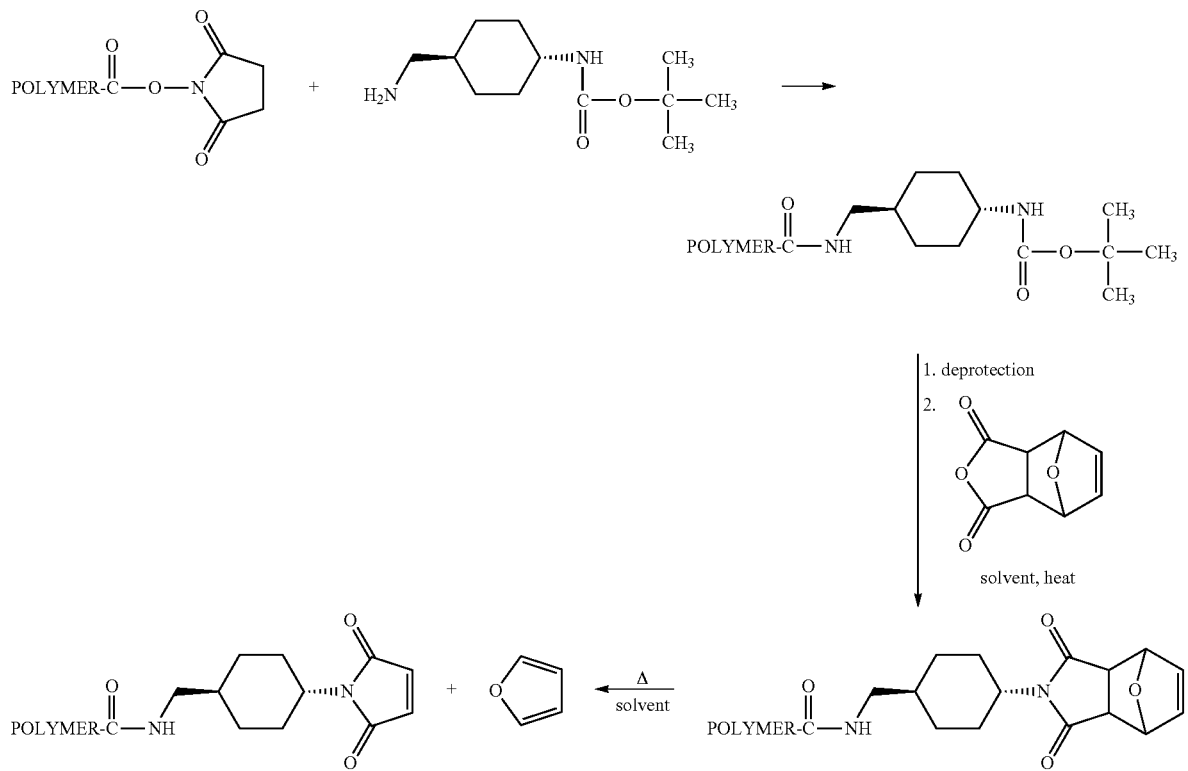

There are some instances where it is desirable to separate the preparation of the maleimide and attachment to the polymer. For example, the maleimide may require special handling or purification or the polymer may be especially costly or complex. As a result, it may be desirable to initiate the retro Diels-Alder reaction to form the maleimide group prior to attachment of the maleimide to the polymer. Reaction Scheme IV below illustrates one example of this embodiment. As shown in Step 1(a), a monoprotected diamine is reacted with a commercially available tricyclic anhydride. In Step 1(b), the resulting product is heated to liberate furan and form the maleimide group, followed by treatment with trifluoroacetic acid (TFA) to deprotect the amine group. Thereafter, the amine group of the maleimide containing structure is reacted with a polymer to form the final product.

Reaction Scheme IV

Step 1

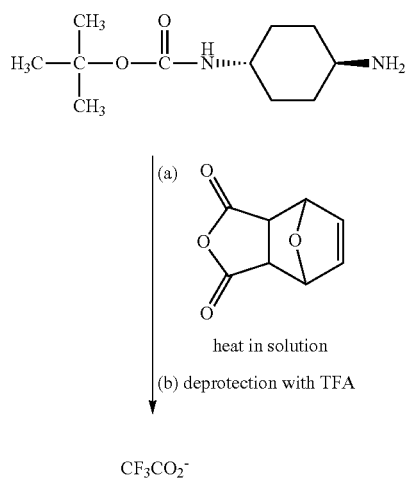

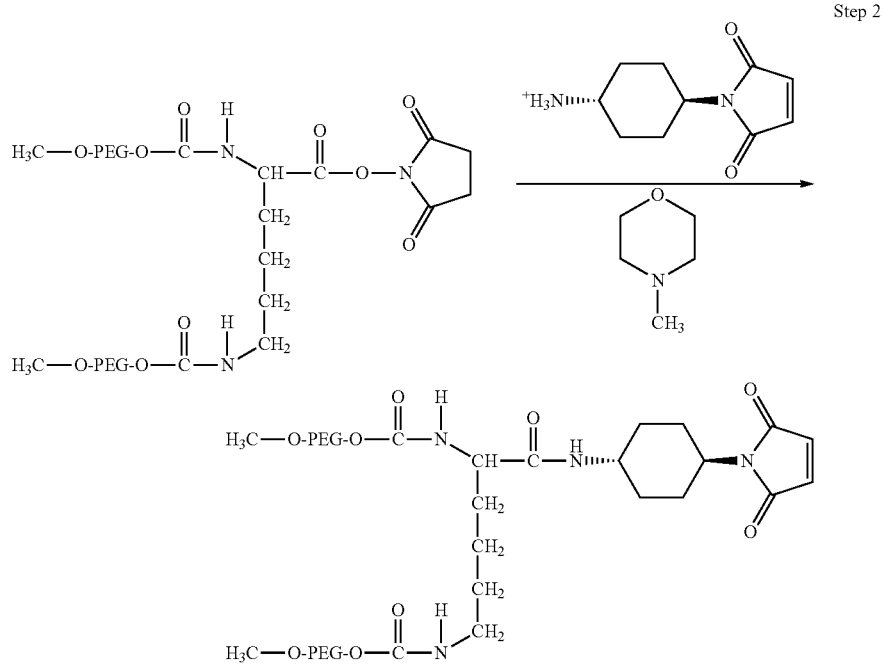

Reaction Scheme V below provides another example of an embodiment of the invention wherein the maleimide is formed prior to attachment to the polymer. In this example, the maleimide-carrying reagent requires activation in order to react with the polymer after the maleimide ring is formed. As shown, a linker molecule comprising an amino group and a carboxylic acid group is reacted with a readily available tricyclic anhydride, which readily liberates furan upon heating to form a maleimide group. Thereafter, the carboxylic acid group is activated by formation of a succinimidyl ester, which is then reacted with an amine-terminated PEG polymer to form the final polymer product.

Reaction Scheme V

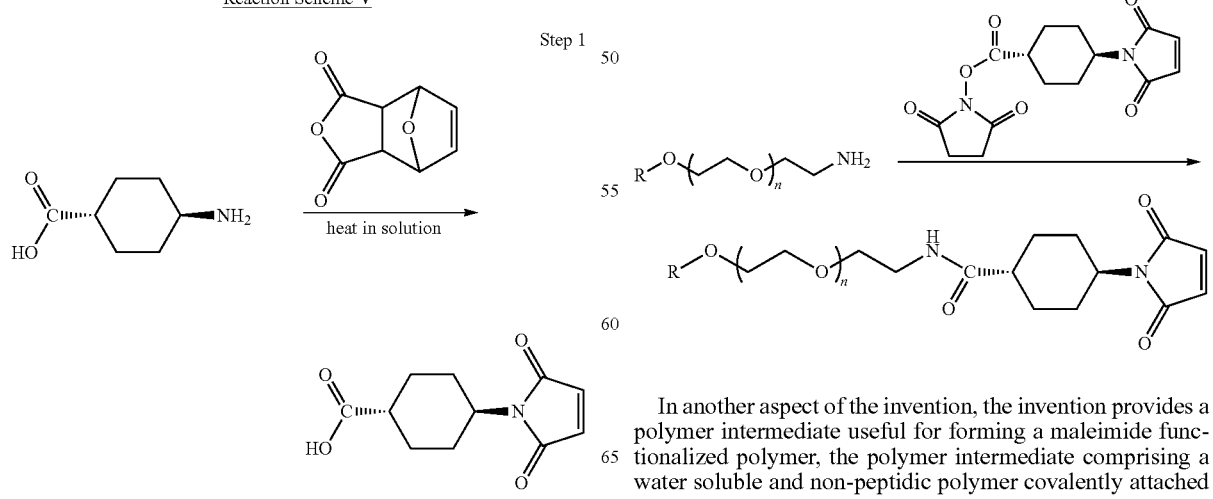

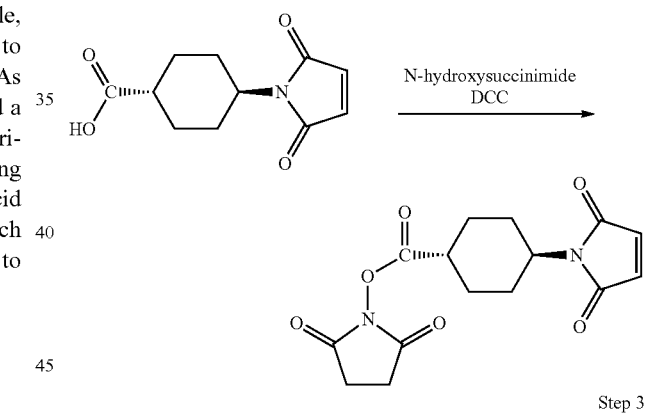

In another aspect of the invention, the invention provides a polymer intermediate useful for forming a maleimide functionalized polymer, the polymer intermediate comprising a water soluble and non-peptidic polymer covalently attached to at least one Diels-Alder adduct, preferably through a hydrolytically stable linkage. The Diels-Alder adduct is preferably a tricyclic imide comprising about 10 to about 20 total ring atoms, with one or two of the ring atoms being independently selected heteroatoms (e.g., NH, S, or O). The tricyclic imide derivative is preferably capable of releasing a cyclic diene in a retro Diels-Alder reaction. Exemplary cyclic dienes include cyclopentadiene, benzene, anthracene, furan, isobenzofuran, isoindole, isophosphindole, thiophene, pyrrole, and selenophene, wherein the cyclic diene may be substituted or unsubstituted at each ring atom position.

The polymer intermediate preferably has the structure:

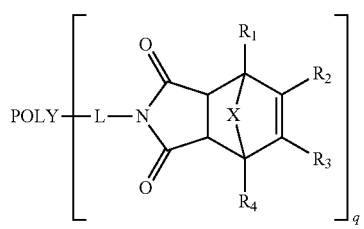

(I)

wherein:

X is an optional alkylene (e.g., C1-C5 alkylene), substituted alkylene, alkenylene (e.g., C2-5 alkenylene with 1 or 2 sites of alkenyl unsaturation), substituted alkenylene, arylene (e.g., 1,2-phenylene), substituted arylene, —C(O)—, or heteroatom (e.g., —O—, —NH—, —S—, —AsH—, —Se—, and —PH—);

each of $R_1$, $R_2$, $R_3$ and $R_4$ is independently selected from the group consisting of H, halo, hydroxyl, carboxyl, carboxylalkyl, thiol, alkylthio, acyl, acyloxy, nitro, cyano, azido, trihalomethyl, alkyl (e.g., C1-C6 alkyl), substituted alkyl, cycloalkyl (e.g., C3-C8 cycloalkyl), substituted cycloalkyl, alkoxy (e.g., C1-C6 alkoxy), aryl (e.g., C6-C12 aryl rings), substituted aryl, heterocycle (e.g., 5- or 6-membered rings), substituted heterocycle, heteroaryl (e.g., 5- or 6-membered rings), and substituted heteroaryl, or $R_2$ and $R_3$, together with the carbon atoms attached thereto, form a 6-membered aryl ring (i.e., a benzene ring);

POLY is a water soluble and non-peptidic polymer, such as PEG;

L is an optional linkage, which is preferably hydrolytically stable; and q is the number of Diels-Alder adducts attached to the polymer, POLY, which is generally roughly equal to the number of termini of the polymer, and which is typically an integer ranging from 1 to about 100, preferably from 1 to about 50, more preferably 1 to about 25, and most preferably 1 to about 10 (e.g., 1, 2, 3, 4, 5, 6, 7, 8, 9 or 10).

Preferred substituting groups of X or $R_1$-$R_4$ include halo, hydroxyl, carboxyl, carboxylalkyl, thiol, alkylthio, acyl, acyloxy, nitro, cyano, azido, trihalomethyl, C1-C6 alkyl, C3-C8 cycloalkyl, C1-C6 alkoxy, and C6-C12 aryl.

In certain preferred embodiments, X is either not present (i.e., hydrogen atoms are instead attached to the carbon atoms bearing $R_1$ and $R_4$) or X is O, S, NH, N-alkyl (including N-cycloalkyl), N-aryl or $CH_2$. In these embodiments, the liberated diene is 1,3-butadiene, furan, thiophene, pyrrole, N-alkyl pyrrole (including N-cycloalkyl pyrrole), N-aryl pyrrole and cyclopentadiene, respectively.

A preferred polymer intermediate has the structure

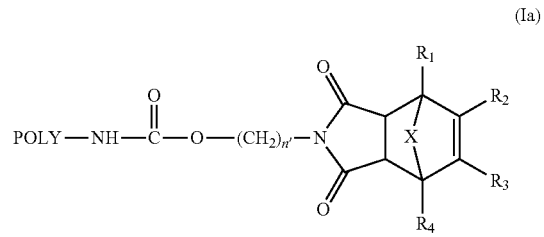

(Ia)

wherein n' is 2 to 10, and each of POLY, $R_1$, $R_2$, $R_3$, $R_4$ and X is as previously defined with respect to Formula (I).

Following the retro Diels-Alder reaction, the maleimide functionalized polymer product will have the generalized structure shown below:

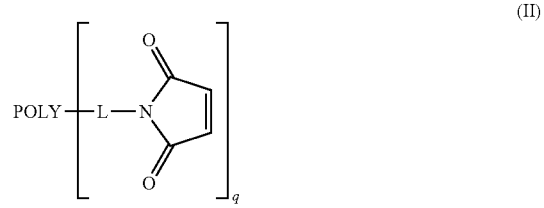

(II)

wherein POLY, L and q are as defined above.

An exemplary maleimide functionalized polymer comprises the following structure:

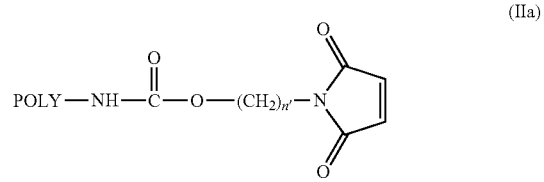

(IIa)

wherein POLY is a water soluble and non-peptidic polymer and n' is 2 to about 10 (e.g., 2, 3, 4, 5, 6, 7, 8, 9 and 10).

Another example of a preferred maleimide functionalized polymer comprises the following structure:

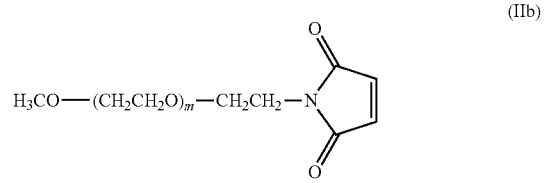

(IIb)

wherein m is from 3 to 3000.

Compositions comprising the maleimide functionalized polymer of Formula (II), (IIa) and (IIb) (or any other maleimide functionalized polymer) will have a certain purity of the maleimide functionalized polymer. Exemplary purities of such compositions include at least 80%, at least 85%, at least 90%, at least 95%, at least 96%, at least 97%, at least 98%, and at least 99% by weight of the maleimide functionalized polymer (as well as any intermediate used in preparing the maleimide functionalized polymer. Stated differently, the maleimide functionalized polymers produced by the present invention are present in a composition having a purity of one of the following values: at least 80%, at least 85%, at least 90%, at least 95%, at least 96%, at least 97%, at least 98%, and at least 99% by weight of the maleimide functionalized polymer (intact ring form).

The maleimide functionalized polymers of the invention are preferably hydrolytically stable over a wide pH range, such as from about 4.5 to about 9.5. In particular, preferred embodiments of the reactive polymers of the invention are hydrolytically stable at a suitable pH for conjugation to thiol or amino groups on biologically active molecules, such as proteins. For example, the reactive polymers of the invention are preferably hydrolytically stable against maleimide ring opening (i.e., stable against formation of a maleamic acid if unconjugated or formation of a succinamidic acid if conjugated) at a pH of about 7 to about 9, more preferably about 7 to about 8. As defined herein, a hydrolytically stable maleimide is one in which the half-life of the maleimide at 25° C. and pH of 7.5 in an aqueous medium is at least about 15 hours, more preferably at least about 21 hours, most preferably at least about 28 hours. The half-life of the maleimide can be determined by measuring the concentration of the maleimide-terminated polymer over time using HPLC techniques known in the art. Hydrolytic stability of the polymer can be increased by manipulation of the linkage between the polymer and the maleimide ring as discussed in greater detail below.

A. Water Soluble and Non-Peptidic Polymers

As used herein, the term "water soluble polymer" includes those water soluble polymers that are biocompatible and non-immunogenic and specifically excludes any water soluble polymer segments that are not biocompatible and nonimmunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water soluble polymer segments described herein as well as conjugates are biocompatible and nonimmunogenic.

When referring to the polymer, it is to be understood that the polymer can be any of a number of water soluble and non-peptidic polymers, such as those described herein as suitable for use in the present invention. Preferably, poly (ethylene glycol) (i.e., PEG) is the polymer. The term PEG includes poly(ethylene glycol) in any of a number of geometries or forms, including linear forms, branched or multi-arm forms (e.g., forked PEG or PEG attached to a polyol core), pendant PEG, or PEG with degradable linkages therein, to be more fully described below. The polymer comprises at least one functional group capable of reacting with the Diels-Alder adduct reagent.

The number of functional groups carried by the polymer and the position of the functional groups may vary. Typically, the polymer will comprise 1 to about 25 functional groups, preferably 1, 2, 3, 4, 5, 6, 7, 8, 9, or 10 functional groups. Linear polymers, such as PEG polymers, will typically comprise one or two functional groups positioned at the terminus of the polymer chain. If the PEG polymer is monofunctional (i.e., mPEG), the polymer will include a single functional group. If the PEG polymer is difunctional, the polymer may contain two independently selected functional groups, one at each terminus of the polymer chain. As would be understood, multi-arm or branched polymers may comprise a greater number of functional groups. In those cases where there are multiple functional groups, each functional group may be reactive or non-reactive toward the Diels-Alder reactant. Thus product polymers may contain reactive functional groups or protected functional groups that are not consumed or involved during the reaction of the polymer component with the Diels-Alder component and are thus available for some other purpose and thereby result in a heterobifunctional polymer.

Multi-armed or branched PEG molecules, such as those described in U.S. Pat. No. 5,932,462, which is incorporated by reference herein in its entirety, can also be used as the PEG polymer. Generally speaking, a multi-armed or branched polymer possesses two or more polymer "arms" extending from a central branch point. For example, an exemplary branched PEG polymer has the structure:

(III)

wherein $PEG_1$ and $PEG_2$ are PEG polymers in any of the forms or geometries described herein, and which can be the same or different, and L' is a hydrolytically stable linkage. An exemplary branched PEG of Formula VI has the structure:

(IV)

wherein $poly_a$ and $poly_b$ are PEG backbones, such as methoxy poly(ethylene glycol); R" is a nonreactive moiety, such as H, methyl or a PEG backbone; and P and Q are nonreactive linkages. In a preferred embodiment, the branched PEG polymer is methoxy poly(ethylene glycol) disubstituted lysine.

The branched PEG structure of Formula VI can be attached to a third oligomer or polymer chain as shown below:

(V)

wherein $PEG_3$ is a third PEG oligomer or polymer chain, which can be the same or different from $PEG_1$ and $PEG_2$.

In another multi-arm embodiment, the polymer comprises a central core molecule derived from a polyol or polyamine, the central core molecule providing a plurality of attachments sites suitable for covalently attaching polymer arms to the core molecule in order to form a multi-arm polymer structure. An exemplary multi-arm polymer of this type has the structure:

$R(\text{-L''-PEG-OH})_q$ (VI)

wherein:

R is the hydrocarbon chain of the polyol or polyamine core molecule, typically comprising about 3 to about 150 carbon atoms, preferably about 3 to about 50 carbon atoms, and most preferably about 3 to about 10 carbon atoms (e.g., 3, 4, 5, 6, 7, 8, 9, or 10), optionally substituted with one or more heteroatoms (e.g., O, S, or N) in the hydrocarbon chain, and which may be linear or cyclic;

L" is a linkage formed from reaction of the polyol or polyamine core molecule with the polymer arms (e.g., —O— or —NH—C(O)—);

PEG is a poly(ethylene glycol) polymer segment; and q is an integer from 3 to abut 25, more preferably 3 to about 10, most preferably 3 to about 8 (e.g., 3, 4, 5, 6, 7, or 8).

The central core molecule in the multi-arm embodiment described above is derived from a molecule that provides a number of polymer attachment sites equal to the desired number of water soluble and non-peptidic polymer arms. Preferably, the central core molecule of the multi-arm polymer structure is the residue of a polyol bearing at least three hydroxyl groups available for polymer attachment or, in a less preferred embodiment, a polyamine bearing at least three amino groups available for polymer attachment. A "polyol" is a molecule comprising a plurality of available hydroxyl groups. A "polyamine" is a molecule comprising a plurality of available amino groups. Depending on the desired number of polymer aims, the polyol or polyamine will typically comprise 3 to about 25 hydroxyl or amino groups, preferably 3 to about 10, most preferably 3 to about 8 (e.g., 3, 4, 5, 6, 7, or 8). The polyol or polyamine may include other protected or unprotected functional groups as well without departing from the invention. Although the spacing between hydroxyl or amino groups will vary, there is typically 1 to about 20 atoms, such as carbon atoms, between each hydroxyl or amino group, preferably 1 to about 5. The particular polyol or polyamine chosen will depend on the desired number of hydroxyl or amino groups needed for attachment to the polymer arms.

The polyol or polyamine core will typically have the structure R—(OH)$_p$ or R—(NH$_2$)$_p$ prior to reaction with the polymer arms, wherein R is a hydrocarbon chain, typically comprising about 3 to about 150 carbon atoms, preferably about 3 to about 50 carbon atoms, and most preferably about 3 to about 10 carbon atoms (e.g., 3, 4, 5, 6, 7, 8, 9, or 10), optionally substituted with one or more heteroatoms (e.g., O, S, or N) in the hydrocarbon chain, and which may be linear or cyclic, and p is the number of hydroxyl or amino groups and is typically 3 to about 25, preferably 3 to about 10, and more preferably 3 to about 8 (e.g., 3, 4, 5, 6, 7, or 8).

Polyols that are suitable for use as the polymer core are nearly limitless. Aliphatic polyols having from 1 to about 10 carbon atoms and from 1 to about 10 hydroxyl groups may be used, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. More examples of aliphatic polyols include derivatives of glyceraldehyde, glucose, ribose, mannose, galactose, and related stereoisomers. Aromatic polyols may also be used, such as 1,1,1-tris(4'-hydroxyphenyl) alkanes, such as 1,1,1-tris(4-hydroxyphenyl)ethane, (1,3-adamantanediyl)diphenol, 2,6-bis(hydroxyalkyl)cresols, 2,2'alkylene-bis(6-t-butyl-4-alkylphenols), 2,2'-alkylene-bis(t-butylphenols), catechol, alkylcatechols, pyrogallol, fluoroglycinol, 1,2,4-benzenetriol, resorcinol, alkylresorcinols, dialkylresorcinols, orcinol monohydrate, olivetol, hydroquinone, alkylhydroquinones, 1,1-bi-2-naphthol, phenyl hydroquinones, dihydroxynaphthalenes, 4,4'-(9-fluorenylidene)-diphenol, anthrarobin, dithranol, bis(hydroxyphenyl) methane biphenols, dialkylstilbesterols, bis(hydroxyphenyl)alkanes, bisphenol-A and derivatives thereof, meso-hexesterol, nordihydroguaiaretic acid, calixarenes and derivatives thereof, tannic acid, and the like. Other core polyols that may be used include crown ether, cyclodextrins, dextrins and other carbohydrates (e.g., monosaccharides, oligosaccharides, and polysaccharides, starches and amylase).

Preferred polyols include glycerol, sugars such as sorbitol or pentaerythritol, and glycerol oligomers, such as hexaglycerol. A 21-arm polymer can be synthesized using hydroxypropyl-β-cyclodextrin, which has 21 available hydroxyl groups.

Polyamines are less preferred for use in the invention due to the reactivity of amino groups with maleimides. However, exemplary polyamines include aliphatic polyamines such as diethylene triamine, N,N',N"-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methylamine, and N,N-dimethyl-dipropylene-triamine. Naturally occurring polyamines that can be used in the present invention include putrescine, spermidine, and spermine. Numerous suitable pentamines, tetramines, oligoamines, and pentamidine analogs suitable for use in the present invention are described in Bacchi et al., *Antimicrobial Agents and Chemotherapy*, January 2002, p. 55-61, Vol. 46, No. 1, which is incorporated by reference herein.

The PEG polymer can alternatively comprise a forked PEG. Generally speaking, a polymer having a forked structure is characterized as having a polymer chain attached to two or more functional groups via covalent linkages extending from a hydrolytically stable branch point in the polymer. An example of a forked PEG is represented by PEG-YCHZ$_2$, where Y is a linking group and Z is an activated terminal group for covalent attachment to a biologically active agent. The Z group is linked to CH by a chain of atoms of defined length. U.S. Pat. No. 6,362,254, the contents of which are incorporated by reference herein, discloses various forked PEG structures capable of use in the present invention. The chain of atoms linking the Z functional groups (e.g., hydroxyl groups) to the branching carbon atom serve as a tethering group and may comprise, for example, an alkyl chain, ether linkage, ester linkage, amide linkage, or combinations thereof.

The PEG polymer may comprise a pendant PEG molecule having reactive groups (e.g., hydroxyl groups) covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more hydrolytically stable or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

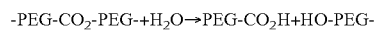

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between acid derivatives and an alcohol; and oligonucleotide linkages formed by, for example, a phosphoramidite group, e.g., at the end of a polymer, and a 5' hydroxyl group of an oligonucleotide. The use of many of the above-described degradable linkages is less preferred due to nucleophilic reactivity of many of the unstable linkages with amine groups.

It is understood by those skilled in the art that the term poly(ethylene glycol) or PEG represents or includes all the above forms of PEG.

Any of a variety of other polymers comprising other non-peptidic and water soluble polymer chains can also be used in the present invention. The polymer can be linear, or can be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxyacetic acid), poly(acrylic acid), poly(vinyl alcohol), polyphosphazene, polyoxazolines, poly(N-acryloylmorpholine), such as described in U.S. Pat. No. 5,629,384, which is incorporated by reference herein in its entirety, and copolymers, terpolymers, and mixtures thereof.

Different polymers can be incorporated into the same polymer backbone. For example, one or more of the PEG molecules in the branched structures shown in Formulas (III)-(VI) can be replaced with a different polymer type. Any combination of water soluble and non-peptidic polymers is encompassed within the present invention.

Although the molecular weight of the water soluble polymer can vary depending on the desired application, the configuration of the polymer structure, the degree of branching, and the like, the molecular weight will satisfy one or more of the following values: greater than 100 Daltons; greater than 200 Daltons; greater than 400 Daltons; greater than 500 Daltons, greater than 750 Daltons; greater than 900 Daltons; greater than 1,000 Daltons, greater than 1,400 Daltons; greater than 1,500 Daltons, greater than 1,900 Daltons; greater than 2,000 Daltons, greater than 2,200 Daltons; greater than 2,500 Daltons, greater than 3,000 Daltons; greater than 4,000 Daltons, greater than 4,900 Daltons; greater than 5,000 Daltons, greater than 6,000 Daltons; greater than 7,000 Daltons, greater than 7,500 Daltons, greater than 9,000 Daltons; greater than 10,000 Daltons, greater than 11,000 Daltons; greater than 14,000 Daltons, greater than 15,000 Daltons; greater than 16,000 Daltons, greater than 19,000 Daltons; greater than 20,000 Daltons; greater than 21,000 Daltons; greater than 22,000 Daltons, greater than 25,000 Daltons; and greater than 30,000 Daltons. It is understood that the maximum limit of molecular weight for any given water soluble polymer segment useful herein is less than about 300,000 Daltons.

The molecular weight of the polymer will typically fall into at least one of the following ranges: from about 100 Daltons to about 100,000 Daltons; from about 200 Daltons to about 60,000 Daltons; from about 300 Daltons to about 40,000 Daltons.

Exemplary molecular weights for the water soluble polymer segment include about 100 Daltons, about 200 Daltons, about 300 Daltons, about 350 Daltons, about 400 Daltons, about 500 Daltons, about 550 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 50,000 Daltons, about 60,000 Daltons, and about 75,000 Daltons.

With respect to branched versions of the polymer, exemplary ranges of suitable sizes for the total molecular weight of the polymer (as based essentially on the combined weights of the two water soluble polymer portions) include the following: from about 200 Daltons to about 100,000 Daltons; from about 1,000 Daltons to about 80,000 Daltons; from about 2,000 Daltons to about 50,000 Daltons; from about 4,000 Daltons to about 25,000 Daltons; and from about 10,000 Daltons to about 40,000 Daltons. More particularly, total weight average molecular weight of a branched version of the polymer of the invention corresponds to one of the following: 400; 1,000; 1,500; 2,000; 3000; 4,000; 10,000; 15,000; 20,000; 30,000; 40,000; 50,000; 60,000; or 80,000.

With respect to PEG, wherein a structure comprising a repeating ethylene oxide monomer, such as "—(CH$_2$CH$_2$O)$_m$—" or "—(OCH$_2$CH$_2$)$_m$—" can be provided, preferred values for (m) include: from about 3 to about 3,000; from about 10 to about 3,000; from about 15 to about 3,000; from about 20 to about 3,000; from about 25 to about 3,000; from about 30 to about 3,000; from about 40 to about 3,000; from about 50 to about 3,000; from about 55 to about 3,000; from about 75 to about 3,000; from about 100 to about 3,000; and from about 225 to about 3,000.

The functional group or groups carried by the polymer will vary, depending on the functional group on the Diels-Alder adduct reagent that is coupled to the polymer. In certain embodiments, the polymer comprises one or more functional groups selected from the following list: active ester (e.g., N-hydroxysuccinimidyl ester and 1-benzotriazolyl ester), active carbonate (e.g., N-hydroxysuccinimidyl carbonate, 1-benzotriazolyl carbonate, p-nitrophenyl carbonate), acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), acid halide, isocyanate, isothiocyanate, maleimide, vinylsulfone, dithiopyridine, vinylpyridine, iodoacetamide, epoxide, biotin, glyoxal, dione, mesylate, tosylate, and tresylate.

In one or more embodiments wherein a linker is attached to the polymer prior to reaction of the polymer with the Diels-Alder adduct reagent, the polymer comprises the formula POLY-L$_3$-Y, wherein POLY is a water soluble and non-peptidic polymer having any of the configurations described above, L$_3$ is a hydrolytically stable linkage, and Y is a functional group reactive with the Diels-Alder adduct reagent, such as an amino group. In this embodiment, the $L_3$ linker forms the linkage, L, of Formulas (I) and (II), which is discussed in greater detail below.

B. Diels-Alder Adduct Reagent

The structure of the Diels-Alder Adduct reagent will depend on a variety of factors, including the general reaction scheme that will be utilized and the desired linkage between the polymer and the maleimide ring of the final product.

In one embodiment, wherein a reaction similar to Reaction Scheme I is utilized, the Diels-Alder adduct reagent is a salt of a tricyclic imide. Preferably, the salt of a tricyclic imide ring has the structure:

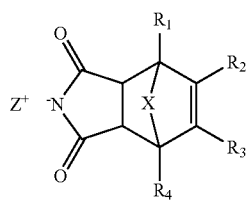

(VII)

wherein $Z^+$ is a counter ion, such as $Na^+$, $NH_4^+$, or $K^+$, and X and $R_1$-$R_4$ are as defined above.

In another embodiment, wherein a reaction similar to Reaction Scheme II is utilized, the Diels-Alder adduct reagent comprises an anhydride ring. An exemplary tricyclic anhydride reagent has the structure:

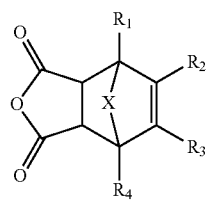

(VIII)

wherein X and $R_1$-$R_4$ are as defined above.

In yet another embodiment, the Diels-Alder adduct reagent includes a linkage structure that becomes part of the linkage between the polymer and the Diels-Alder adduct (or maleimide ring of the final product). In this embodiment, a bicyclic, tricyclic or other polycyclic imide ring or a bicyclic, tricyclic, or other polycyclic anhydride ring is attached to a linker molecule prior to coupling the Diels-Alder adduct to the polymer. An exemplary Diels-Alder adduct reagent structure of this embodiment is given below.

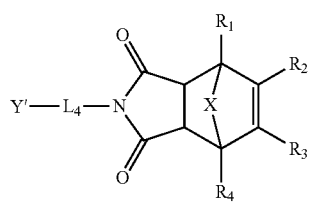

(IX)

wherein:
Y' is a functional group reactive with the functional group of the polymer;
$L_4$ is a hydrolytically stable linkage; and X and $R_1$-$R_4$ are as defined above. In this embodiment, the linker $L_4$ and the linkage resulting from reaction of the Y' functional group of the Diels-Alder adduct reagent with the functional group on the polymer together form the linkage, L, of Formulas (I) and (II), which is described in greater detail below.

The Diels-Alder adduct reagent of Formula (IX) is preferably formed by reaction of a tricyclic anhydride or tricyclic imide with a linker molecule having the structure A-$L_2$-B, wherein: A [which will ultimately correspond to Y' in Formula (IX)] is a functional group reactive with a functional group on the polymer in order to form a hydrolytically stable linkage between the linker reagent and the polymer (i.e., capable of reacting to form $L_1$ described below); B is a functional group reactive with the desired tricyclic reagent [e.g., an amino group that reacts with an anhydride to form an imide or an alkyl halide or mesylate that reacts with Formula (VII)]; and $L_2$ is the hydrocarbon linkage described in greater detail below.

Examples of functional groups useful as A [which will ultimately correspond to Y' in Formula (IX)] in linker molecule A-$L_2$-B include halo, active ester (e.g., N-hydroxysuccinimidyl ester and 1-benzotriazolyl ester), active carbonate (e.g., N-hydroxysuccinimidyl carbonate, 1-benzotriazolyl carbonate, p-nitrophenyl carbonate), acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), acid halide, isocyanate, isothiocyanate, maleimide, vinylsulfone, dithiopyridine, vinylpyridine, iodoacetamide, epoxide, biotin, glyoxal, dione, mesylate, tosylate, and tresylate. In some instances, a protecting group can protect the functional group, A, so that unwanted side reactions are minimized as the linker molecule A-$L_2$-B is reacted with the desired tricyclic reagent to provide a compound having the structure of Formula (IX).

Specific examples of linker precursors include 1,4-dibromobutane, 1,5-dibromopentane, 1,6-dibromohexane, 4,7,10-trioxa-1,3-tridecanediamine, tetramethylenediamine, pentamethylenediamine, hexamethylenediamine, 2,5-diamino-2,5-dimethylhexane, 1,3-cyclohexylbis(methylamine), and 1,4-cyclohexylbis(methylamine). Note that the diamine reagents described above are typically used in monoprotected form, meaning one of the amine groups is initially in protected form when the linker molecule is coupled with the desired tricyclic reagent. The linker molecules used in the invention are either commercially available, for example from Pierce Chemical Company, Rockford, Ill., or can be prepared from commercially available starting materials using methodology known in the art.

C. Linkage Between the Polymer and Diels-Alder Adduct (or Corresponding Maleimide)

The linkage between the polymer backbone and the Diels-Alder adduct (or the maleimide group following the retro Diels-Alder reaction), referred to as "L" in Formulas (I) and (II), is preferably hydrolytically stable and is dependent upon the structure of the polymer and Diels-Alder adduct reagent used to form the polymer comprising a Diels-Alder Adduct (or corresponding maleimide). As noted above, the linkage is optional, meaning the Diels-Alder adduct (or corresponding maleimide) can be directly attached to the terminal hydrocarbon group of the polymer, which in the case of PEG, is an ethylene group. However, due to the susceptibility of the maleimide group to ring opening in aqueous media, it is often desirable to increase the hydrolytic stability of the maleimide ring through the use of a stabilizing linkage between the polymer and the maleimide ring.

In one preferred embodiment, the linkage comprises a saturated acyclic or alicyclic hydrocarbon moiety adjacent to the nitrogen atom of the maleimide (or Diels-Alder adduct). The size and structure of the saturated acyclic or alicyclic hydrocarbon moiety is selected so as to increase the hydrolytic stability of the maleimide ring by increasing the distance between the maleimide ring and any electron withdrawing groups (e.g., carbonyl and oxygen) present in the molecule, or by providing steric hindrance to the hydrolysis reaction.

Exemplary hydrocarbon linkages include straight chain saturated acyclic hydrocarbons comprising at least three carbon atoms, such as trimethylene, tetramethylene, pentamethylene, and hexamethylene, as well as branched saturated acyclic hydrocarbons comprising at least three carbon atoms. In one embodiment, the hydrocarbon portion of the linkage has the structure $-(CR_1R_2)_m-$, wherein $R_1$ and $R_2$ are each independently H, alkyl, or cycloalkyl, and m is 1 to about 20, preferably 3 to about 12. In one preferred embodiment, $R_1$ and $R_2$ are H. In branched acyclic hydrocarbon embodiments, it is preferable for the branching to occur at one or more of the two carbon atoms closest to the maleimide ring in order to maximize steric hindrance. In another embodiment, the hydrocarbon portion of the linkage includes a saturated bivalent alicyclic hydrocarbon and has the structure $-(CR_1R_2)_p-C3-C12cycloalkyl-(CR_1R_2)_q-$, wherein each of p and q is independently 0 to about 10, preferably 0 to about 6 (e.g., 0, 1, 2, 3, 4, 5, or 6). The bivalent cycloalkyl group is preferably C3-C8cycloalkyl, such as cyclopropadiyl, cyclobutadiyl, cyclopentadiyl, cyclohexadiyl, and cycloheptadiyl. The cycloalkyl group can be substituted with one or more alkyl groups, preferably C1-C6alkyl groups.

The linkage, L, may further include a non-hydrocarbon portion adjacent to the polymer. In such embodiments, the L linkage will have the structure -$L_1$-$L_2$-, wherein $L_1$ is the non-hydrocarbon portion of the linkage adjacent to the polymer and $L_2$ is the hydrocarbon portion of the linkage adjacent to the maleimide and described above. The non-hydrocarbon portion of the linkage, $L_1$, typically results from reaction of a functional group attached to the polymer backbone with a functional group on a linker molecule or a functional group on a Diels-Alder adduct reagent comprising a linker segment as depicted in Formula (IX) above (i.e., $L_1$ is the result of reaction of the Y' functional group of Formula (IX) with the polymer). The specific non-hydrocarbon linkage will depend on the type of functional groups utilized. In embodiments wherein the functional group on the polymer backbone is hydroxy and the functional group on the linker reagent is a leaving group, such as halogen, the linkage will be O. If the functional group on the polymer is an amino group and the functional group on the linker reagent is N-succinimidyl ester, the linkage will be amide. Preferably, the linkage is a hydrolytically stable linkage, such as heteroatom linkages (e.g., ether or thioether), amide, amine, urethane, and urea. The overall length of the non-hydrocarbon portion ("$L_1$") will typically vary between 1 to about 20 atoms, preferably 1 to about 10 atoms, more preferably 1 to about 5 atoms.

Optionally, the linkage (whether defined, for example, as simply "L" or "-$L_1$-$L_2$-") can include one or more atoms such as a lower alkyl chain, preferably C1-C6alkyl (e.g., methylene, ethylene, and so forth). In addition, the linkage can also include one more ethylene glycol oligomers (e.g., an oligomer having 1, 2, 3, 4, 5, 6, 7 or 8 ethylene oxide units). Preferred linkages (particularly "$L_1$" linkages) include —O—, —S—, —NH—C(O)—, —C(O)—NH—, —NH—, —CH$_2$—C(O)—NH—, and —O—C(O)—NH—.

Exemplary linkages, as well as exemplary atom(s) that may be positioned adjacent to a linkage such as "$L_1$", and/or "$L_2$" include the following: —O—, —S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—, —CH$_2$—NH—C(O)—CH$_2$—, —CH$_2$—CH$_2$—CH$_2$—C(O)—NH—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, —O—C(O)—CH$_2$—CH$_2$—CH$_2$—, —CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —CH$_2$—CH$_2$—CH$_2$—C(O)—NH—CH$_2$—CH$_2$—NH—C(O)—CH$_2$—, O—C(O)—NH—[CH$_2$]$_f$—(OCH$_2$CH$_2$)$_n$—, and combinations of two or more of any of the foregoing, wherein (f) is 0 to 6, (n) is 0 to 20 (preferably 0 to 10, e.g., 0, 1, 2, 3, 4, 5, 6, 7, 8, 9 or 10, and more preferably 4). Nonlimiting examples of bivalent cycloalkyl (e.g., cycloalkylene) groups include $C_{3-8}$ cycloalkyl, such as various isomers of cyclopropadiyl (e.g., 1,1-, cis-11,2-, or trans-1,2-cyclopropylene), cyclobutadiyl, cyclopentadiyl, cyclohexadiyl, and cycloheptadiyl. The cycloalkylene group can be substituted with one or more alkyl groups, preferably $C_1$-$C_6$ alkyl groups.

The invention also provides certain other compounds that are useful as intermediates or regents in accordance with one or more of the methods described herein.

In this regard, one compound comprises the following structure:

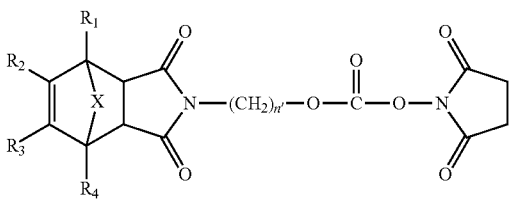

wherein:

X is selected from the group consisting of alkylene, substituted alkylene, alkenylene, substituted alkenylene, —C(O)—, heteroatom and substituted heteroatom;

each of $R_1$, $R_2$, $R_3$ and $R_4$ is independently selected from the group consisting of H, halo, hydroxyl, carboxyl, carboxylalkyl, thiol, alkylthio, acyl, acyloxy, nitro, cyano, azido, trihalomethyl, alkyl, substituted alkyl, cycloalkyl, substituted cycloalkyl, alkoxy, aryl, substituted aryl, heterocycle, substituted heterocycle, heteroaryl, and substituted heteroaryl; and n' is 2 to about 10.

Another compound comprises the following structure:

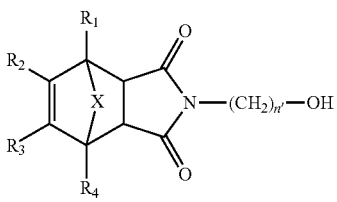

wherein:

X is selected from the group consisting of alkylene, substituted alkylene, alkenylene, substituted alkenylene, —C(O)—, heteroatom and substituted heteroatom;

each of $R_1$, $R_2$, $R_3$ and $R_4$ is independently selected from the group consisting of H, halo, hydroxyl, carboxyl, carboxylalkyl, thiol, alkylthio, acyl, acyloxy, nitro, cyano, azido, trihalomethyl, alkyl, substituted alkyl, cycloalkyl, substituted cycloalkyl, alkoxy, aryl, substituted aryl, heterocycle, substituted heterocycle, heteroaryl, and substituted heteroaryl; and n' is 4 to about 10.

Still another compound comprises the structure:

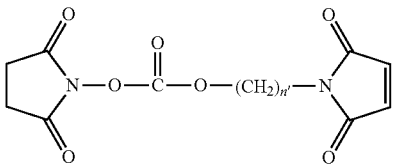

wherein n' is 2 to about 10.

D. Biologically Active Conjugates

The present invention also includes stabilized biologically active conjugates comprising a nucleophilic biologically active molecule capable of Michael addition covalently attached to the reactive polymer through a succinimide ring linkage. The biologically active agent is preferably a protein bearing a thiol or amino group. In certain embodiments, a saturated acyclic or alicyclic hydrocarbon adjacent to the succinimide ring of the conjugate stabilizes the succinimide ring from ring opening resulting from hydrolysis in the same manner that the hydrocarbon structure stabilizes the maleimide ring in the reactive polymers described above.

Suitable biologically active agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Examples of active agents suitable for use in covalent attachment to the reactive polymer of the invention include, but are not limited to, calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., monoacylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining stability and other parameters of the composition, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with a conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the patient as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains. Although specific terms are employed herein, they are used in a generic and descriptive sense only and not for purposes of limitation.

All articles, books, patents and other publications referenced herein are hereby incorporated by reference in their entireties.

EXPERIMENTAL

Example 1

Preparation of 2-Hydroxyethylmaleimide-Furan Adduct (HEMI-A or N-hydroxyethyl exo-3,6-epoxy-1,2,3,6-tetrahydrophthalimide)

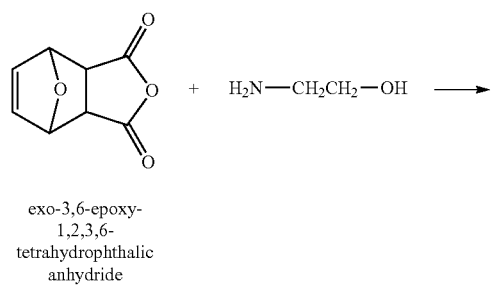

exo-3,6-epoxy-
1,2,3,6-
tetrahydrophthalic
anhydride

N-hydroxyethyl exo-3,6-epoxy-
1,2,3,6-tetrahydrophthalimide
(HEMI-A)

To a solution of exo-3,6-epoxy-1,2,3,6-tetrahydrophthalic anhydride (Sigma-Aldrich, St. Louis Mo.; 30.0 g, 0.181 moles) in anhydrous ethyl alcohol (40 mL), a solution of ethanolamine (12.6 g, 0.206 moles) in anhydrous ethyl alcohol (10 mL) was added over a time period of 2 hours to form a mixture. The mixture was then refluxed for about 3.5 hours and was cooled to room temperature and left to stand overnight. The precipitated product that formed during overnight standing was filtered off and washed with 20 mL of anhydrous ethyl alcohol. The collected solid was then dried under reduced pressure giving 18.3 g of white crystals. NMR ($d_6$-DMSO): 2.92 ppm (s, —CH, 2H), 3.41 ppm (m, —CH$_2$CH$_2$—, 4H), 4.77 ppm (bm, —OH, 1H), 5.12 ppm (s, —CH, 2H), 6.55 ppm (s, —CH=CH—, 2H). Purity: ~100%.

Example 2

Preparation of Succinimidyl Carbonate of 2-Hydroxyethylmaleimide-Furan Adduct (HEMI-A-SC)

HEMI-A

HEMI-A-SC

To a solution of HEMI-A (2.0 g, 0.0095 moles) in anhydrous acetonitrile (30 mL), was added anhydrous pyridine (1.0 mL, 0.0124 moles) and N,N-disuccinimidyl carbonate (DSC, 2.43 g, 0.0095 moles). The resulting mixture was stirred overnight at room temperature under a nitrogen atmosphere. The precipitated product that formed during the overnight reaction was filtered off and washed with 5 mL of acetonitrile. The collected solid was dried under vacuum giving 2.68 g of white crystals. NMR ($d_6$-DMSO): 2.79 ppm (s, —CH$_2$CH$_2$—, succinimide, 2H), 2.96 ppm (s, —CH, 2H), 3.72 ppm (t, —CH$_2$—N, 2H), 4.41 ppm (t, —C$\underline{H}_2$CH$_2$—N, 2H), 5.15 ppm (s, —CH, 2H), 6.56 ppm (s, —CH═CH—, 2H). Purity: ~100%.

Example 3

Preparation of mPEG$_{(5\ KDa)}$-HEMI-A

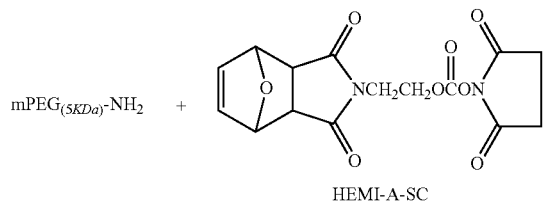

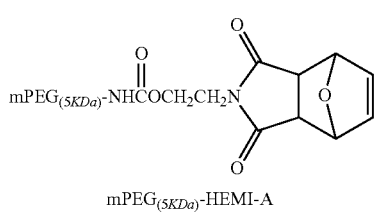

To a solution mPEG$_{(5\ KDa)}$-amine (2.0 g, 0.00040 moles) (Nektar Therapeutics, Huntsville Ala.) in anhydrous acetonitrile (30 mL) was added HEMI-A-SC (0.15 g, 0.00043 moles) and triethylamine (0.050 mL) to form a reaction mixture. The reaction mixture was then stirred overnight at room temperature under an argon atmosphere. Next, the solvent was evaporated to dryness. The crude product was then dissolved in methylene chloride and precipitated with ethyl ether at 0° C. The wet product was dried under reduced pressure to yield 1.9 g of the desired product. NMR (d$_6$-DMSO): 2.92 ppm (s, —CH, 2H), 3.08 ppm (q, —OCH$_2$C$\underline{H}_2$N, 2H), 3.24 ppm (s, —OCH$_3$), 3.51 ppm (s, PEG backbone), 4.00 ppm (t, —CH$_2$(C═O)N, 2H), 5.13 ppm (s, —CH, 2H), 6.55 ppm (s, —CH═CH—, 2H). Substitution of HEMI-A: ~100%.

Example 4

Preparation of mPEG$_{(5\ KDa)}$-Maleimide

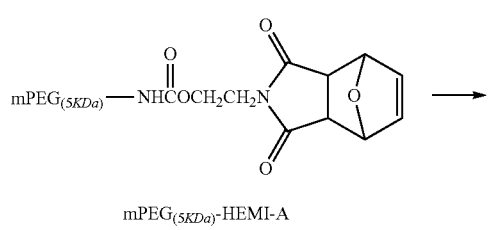

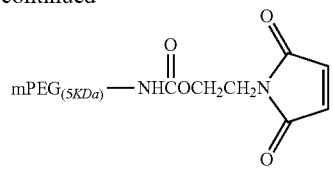

mPEG$_{(5\ KDa)}$-HEMI-A (1.9 g) was dissolved in 20 mL of dry toluene and the solution was heated to reflux for 5 hours under an argon atmosphere. Next, the solution was concentrated under reduced pressure, cooled to room temperature and added to cold ethyl ether. The precipitated product was filtered off and dried under vacuum. Yield 1.7 g. NMR (d$_6$-DMSO): 2.92 ppm (s, —CH, 2H), 3.06 ppm (q, —OCH$_2$C$\underline{H}_2$N, 2H), 3.24 ppm (s, —OCH$_3$), 3.51 ppm (s, PEG backbone), 4.06 ppm (t, —CH$_2$(C═O)N, 2H), 6.98 ppm (s, —CH═CH—, maleimide, 2H), 7.08 ppm (t, —NH, 1H). Substitution of maleimide: ~100%.

Example 5

Preparation of 3,6-Epoxy-1,2,3,6-tetrahydrophthalimide (ETPI)

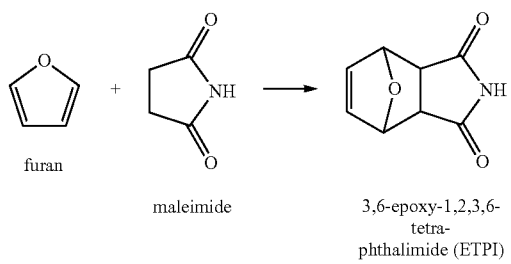 [SMILES: c1ccoc1 ; O=C1CCC(=O)N1 ; O=C1NC(=O)C2C3C=CC(O3)C12]

A mixture of maleimide (Sigma-Aldrich, St. Louis Mo.; 2.0 g, 0.0206 moles) and furan (Sigma-Aldrich, St. Louis Mo.; 7.49 mL, 0.103 moles) in anhydrous ethyl ether (50 mL) was stirred for 70 hours at room temperature under an argon atmosphere. A white precipitate formed during the reaction and was filtered off and dried under reduced pressure giving 1.57 g of white crystals. NMR (d$_6$-DMSO): Mixture of exo- and endo-isomers (37:63) of ETPI: Exo-3,6-Epoxy-1,2,3,6-tetrahydrophthalimide: 2.85 ppm (s, —CH, 2H), 5.25 ppm (s, —CH, 1H), 6.55 ppm (s, —CH═CH—, 2H), Endo-3,6-Epoxy-1,2,3,6-tetrahydrophthalimide: 3.48 ppm (s, —CH, 2H), 5.11 ppm (s, —CH, 2H), 6.49 ppm (s, —CH═CH, 2H).

Example 6

Preparation of mPEG$_{(5\ KDa)}$-ETPI

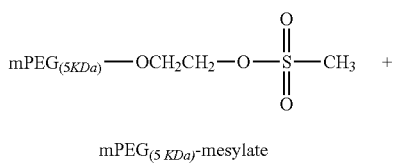

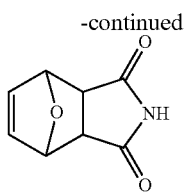

ETPI

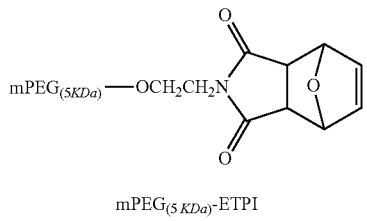

mPEG$_{(5\,KDa)}$-ETPI

To a solution mPEG$_{(5KDa)}$-mesylate (2.0 g, 0.00040 moles) (Nektar Therapeutics, Huntsville Ala.) in anhydrous acetonitrile (20 mL), ETPI from example 4 (0.20 g, 0.00043 moles) and potassium carbonate (2.0 g) were added and the reaction mixture was stirred overnight at 40° C. under argon atmosphere. Next, the mixture was filtered and added to 400 mL of isopropyl alcohol at 0-5° C. The precipitated product was filtered off and dried under reduced pressure. Yield 1.3 g. NMR (d$_6$-DMSO): Desired product [mixture of exo- and endo-isomers (37:63)]: 2.85 ppm (s, —CH, 2H, exo-form), 3.24 ppm (s, —OCH$_3$), 3.51 ppm (s, PEG backbone), 5.12 and 5.19 ppm (s, —CH, 2H, endo- and exo-forms), 6.39 and 6.55 ppm (s, —CH=CH, 2H, endo- and exo-forms). Substitution of ETPI: ~100%.

Example 7

Preparation of mPEG$_{(5KDa)}$-Maleimide

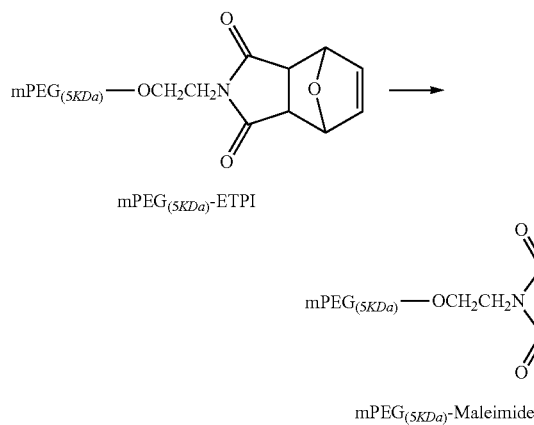

mPEG$_{(5KDa)}$-ETPI (1.9 g) was dissolved in 20 mL toluene and the solution was heated to reflux for 4 hours under an argon atmosphere. The solution was then concentrated under reduced pressure, cooled to room temperature and added to cold ethyl ether. The precipitated product was filtered off and dried under vacuum. Yield 1.7 g. NMR (d$_6$-DMSO): 3.24 ppm (s, —OCH$_3$), 3.51 ppm (s, PEG backbone), 7.02 ppm (s, —CH=CH—, maleimide, 2H). Substitution of maleimide: ~100%. No open chain maleamic acid was detectable by NMR.

Example 8

Preparation of mPEG$_{(5\,KDa)}$-butylbromide

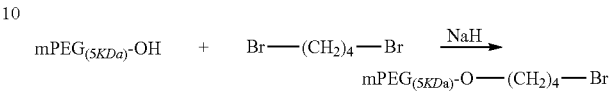

A solution of mPEG-5,000 Da (20.0 g, 0.004 moles) (NOF Corporation, Tokyo, Japan) in toluene (200 mL) was azeotropically dried by distilling off 50 mL toluene. Sodium hydride (0.8 g, 60% dispersion in mineral oil, 0.020 moles) was added and the mixture was stirred for 1 hour at 60° C. under an argon atmosphere. 1,4-Dibromobutane (9.0 g, 0.0417 moles) was added and the mixture was stirred overnight at 75° C. under an argon atmosphere. The mixture was filtered and concentrated under reduced pressure. Next, the concentrated product was added to 850 mL of cold ethyl ether. The precipitated product was filtered off and dried under reduced pressure. Yield 17.4 g. NMR (d$_6$-DMSO): 1.60 ppm (m, —O—CH$_2$—CH$_2$—CH$_2$—CH$_2$—Br, 2H), 1.84 ppm (m, —O—CH$_2$—CH$_2$—CH$_2$—CH$_2$—Br, 2H), 3.24 ppm (s, —OCH$_3$, 3H), 3.51 ppm (s, PEG backbone). Substitution of bromobutane: ~100%.

Example 9

Preparation of mPEG$_{(5\,KDa)}$-O(CH$_2$)$_4$-ETPI

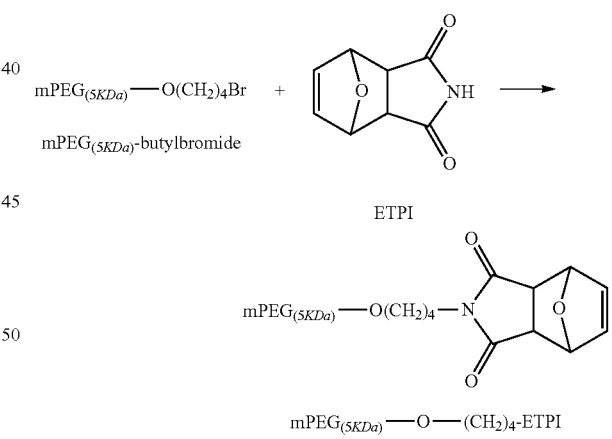

To a solution mPEG$_{(5\,KDa)}$-butylbromide from Example 8 (2.0 g, 0.00040 moles) in anhydrous acetonitrile (20 mL), ETPI from Example 5 (0.20 g, 0.00043 moles) and potassium carbonate (2.0 g) were added to form a reaction mixture. The reaction mixture was stirred overnight at 35° C. under an argon atmosphere. The mixture was then filtered and added to 400 mL of isopropyl alcohol cooled to 0 to 5° C. The precipitated product was filtered off and dried under reduced pressure. Yield 1.3 g. NMR (d$_6$-DMSO): Desired product (mixture of exo- and endo-isomers (37:63)): 1.38 ppm (bm, —CH$_2$—CH$_2$—CH$_2$-ETPI, 4H), 2.91 ppm (s, —CH, 2H, exo-form), 3.24 ppm (s, —OCH$_3$), 3.51 ppm (s, PEG backbone), 5.12 and 5.29 ppm (s, —CH, 2H, endo- and exo-forms), 6.40 and 6.55 ppm (s, —CH═CH, 2H, endo- and exo-forms). Substitution of ETPI: ~100%.

Example 10

Preparation of mPEG$_{(5KDa)}$-Butyl Maleimide

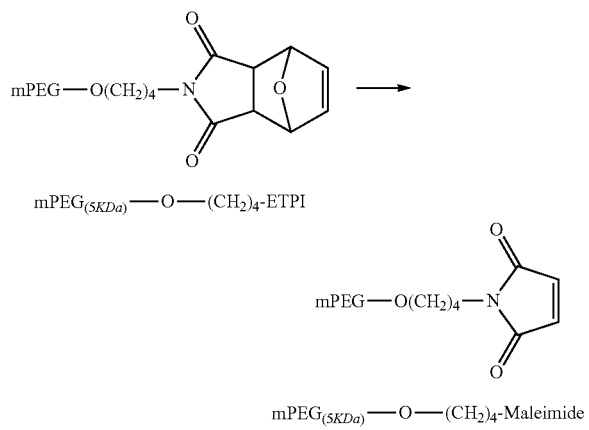

mPEG$_{(5KDa)}$-O—(CH$_2$)$_4$-ETPI (1.9 g) was dissolved in 20 mL toluene and the solution was heated and refluxed for 4 hours under an argon atmosphere. The solution was then concentrated under reduced pressure, cooled to room temperature and added to cold ethyl ether. The precipitated product was filtered off and dried under vacuum. Yield 1.7 g. NMR (d$_6$-DMSO): 1.48 ppm (bm, —CH$_2$—CH$_2$—CH$_2$-Maleimide), 3.24 ppm (s, —OCH$_3$), 3.51 ppm (s, PEG backbone), 7.00 ppm (s, —CH═CH—). Substitution of maleimide: ~100%. No ring-opened maleamic acid product was detectable by NMR.

Example 11

Examples 3 to 10 Carried Out With Different Polymers

Examples 3 to 10 can be carried out with water soluble and non-peptidic polymers having different molecular weights, different geometries, different end-capping groups, and so forth. Such water soluble and non-peptidic polymers are described more fully in the specification.

Example 12

Preparation of a Polymer Bearing a Single Maleimide Group

The potassium salt of a tricyclic imide (shown below) is reacted with an mPEG polymer (available from Nektar Therapeutics, Huntsville Ala.) carrying a mesylate group ("Ms"), resulting in a coupling of the tricyclic imide to the polymer. Thereafter, heat is applied to liberate furan from the Diels-Alder adduct, leaving a maleimide group attached to the polymer.

Schematically, the reaction is depicted below (wherein n is 3 to 3000).

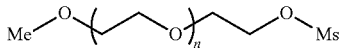

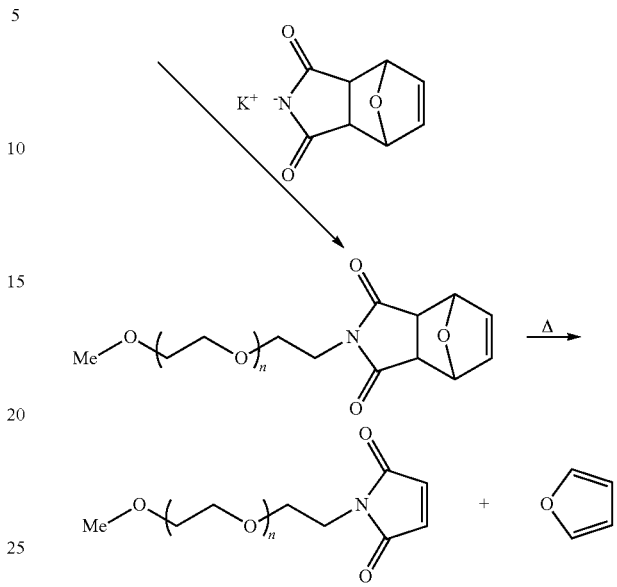

Example 13

Preparation of a Polymer Bearing Two Maleimide Groups

A diamino PEG (Nektar Therapeutics, Huntsville Ala.) is reacted with a tricyclic molecule containing a reactive anhydride group, 7-oxabicyclo[2.2.1]hept-5-ene-2,3-dicarboxylic anhydride, which readily releases furan following reaction with the amine.

Schematically, the reaction can be depicted below.

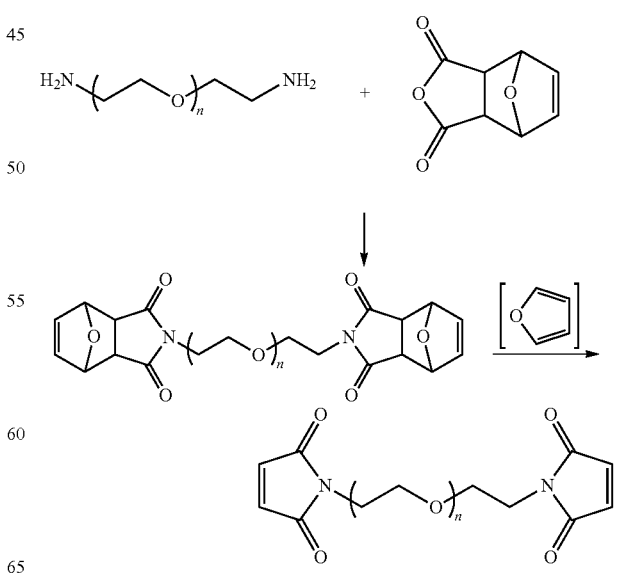

What is claimed is:
1. A compound of the following structure:
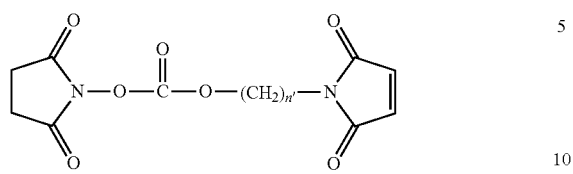
wherein n' is 2 to about 10.
2. The compound of claim 1, wherein n' is 2.
3. The compound of claim 1, wherein n' is 4 to about 10.
4. The compound of claim 1, wherein n' is 4.
* * * * *